United States Patent [19]

Cozzette et al.

[11] Patent Number: 5,112,455
[45] Date of Patent: May 12, 1992

[54] METHOD FOR ANALYTICALLY UTILIZING MICROFABRICATED SENSORS DURING WET-UP

[75] Inventors: Stephen N. Cozzette, Highstown; Graham Davis, Plainsboro; Lisa A. Holleritter, Oak Ridge, all of N.J.; Imants R. Lauks, Yardley, Pa.; Sylvia Piznik, Jackson, N.J.; Nicolaas J. Smit, Woodlawn, Canada; Jody A. Tirinato, Plainsboro, N.J.; Henry J. Wieck, Plainsboro, N.J.; Michael P. Zelin, Plainsboro, N.J.

[73] Assignee: I Stat Corporation, Princeton, N.J.

[21] Appl. No.: 555,976

[22] Filed: Jul. 20, 1990

[51] Int. Cl.$^5$ .................... G01N 27/26; C25F 7/00
[52] U.S. Cl. .................... 204/153.12; 204/153.1; 204/153.17; 204/403; 204/400; 204/402; 204/406
[58] Field of Search .............. 204/153.12, 153.17, 204/153.1, 402, 406, 403, 400, 424

[56] References Cited

U.S. PATENT DOCUMENTS

| | | | |
|---|---|---|---|
| 3,672,843 | 6/1972 | Rosse et al. | 204/433 |
| 3,765,841 | 10/1973 | Paulson et al. | 204/153.12 |
| 4,019,966 | 4/1977 | Remes et al. | 204/402 |
| 4,033,830 | 7/1977 | Fletcher, III | 204/153.1 |
| 4,225,410 | 9/1980 | Pace | 204/153.12 |
| 4,293,522 | 10/1981 | Winkler | 204/424 |
| 4,464,230 | 8/1984 | Langdon | 204/153.17 |
| 4,535,285 | 8/1985 | Evans et al. | 204/153.1 |
| 4,686,479 | 8/1987 | Young et al. | 204/153.1 |
| 4,787,252 | 11/1988 | Jacobson et al. | 73/861.28 |
| 4,886,590 | 12/1989 | Tittle | 204/406 |
| 4,897,162 | 1/1990 | Lewandowski et al. | 204/153.17 |
| 4,933,048 | 6/1990 | Lauks | 204/400 |
| 4,935,105 | 6/1990 | Chuchouse | 204/402 |
| 4,935,106 | 6/1990 | Liston et al. | 204/153.12 |

Primary Examiner—John Niebling
Assistant Examiner—Bruce F. Bell
Attorney, Agent, or Firm—Pennie & Edmonds

[57] ABSTRACT

A method of determining the concentration of a preselected analyte species present in a sample fluid is disclosed, which method comprises: (a) providing an external computational means, a reference electrode and at least one substantially dry-stored sensor capable of exhibiting a response to changes in the concentration of a preselected analyte species before the sensor attains full equilibrated wet-up; (b) establishing electrical contact between the sensor, reference electrode and external computational means; (c) contacting the sensor and reference electrode with a calibrant fluid; (d) performing a first signal measurement in a first time window in the presence of the calibrant fluid; (e) displacing the calibrant fluid after performing the first signal measurement; (f) contacting the sensor and reference electrode with a sample fluid; (g) performing a second signal measurement in a second time window in the presence of the sample fluid; and (h) relating the first and second signal measurements to determine the concentration of the preselected analyte species in the sample fluid before said sensor attains full equilibrated wet-up. Alternative methods are disclosed further for collecting, relating and manipulating the results of the signal measurements to provide useful estimates of the analyte concentrations of interest.

68 Claims, 18 Drawing Sheets

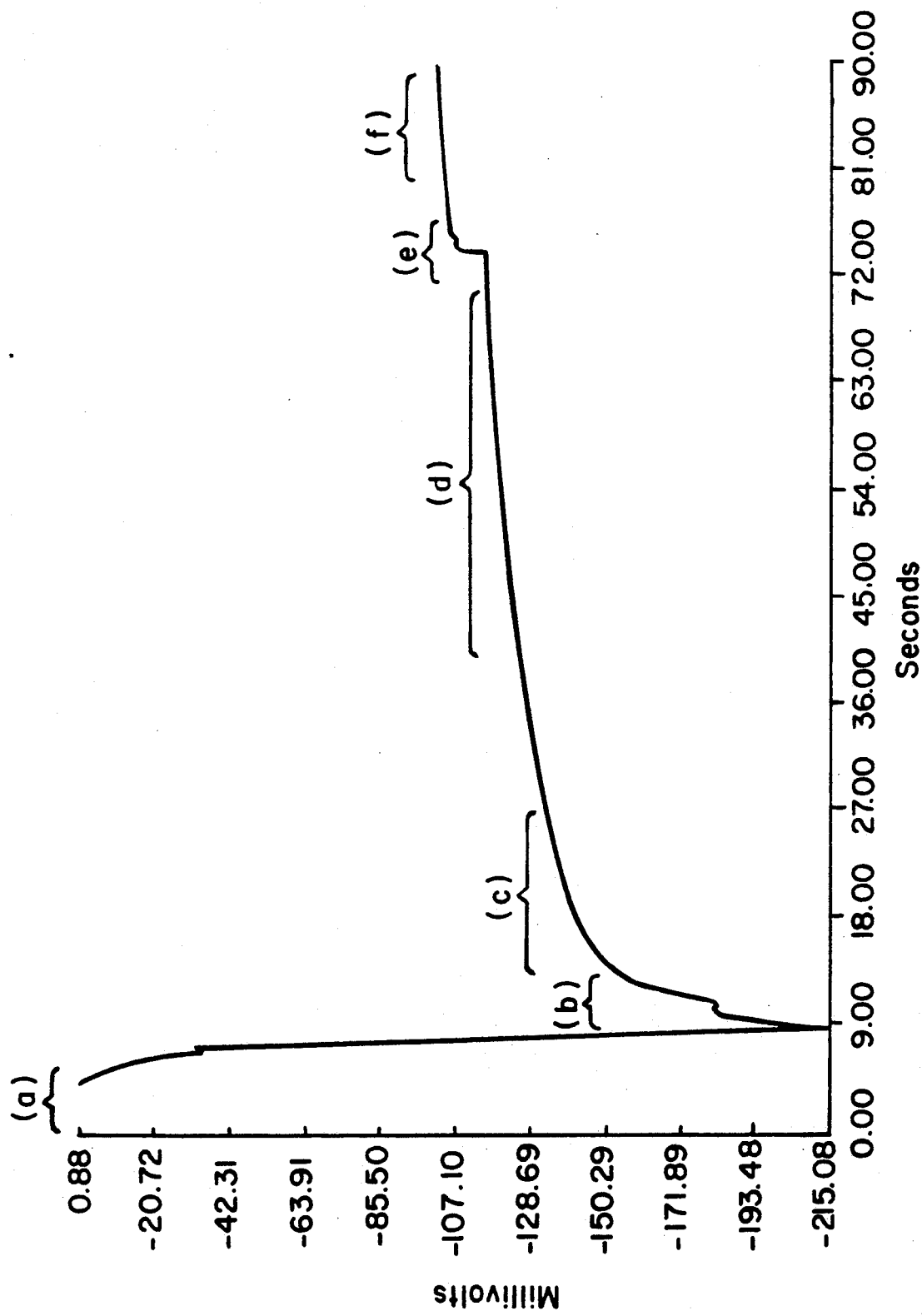

METHOD FOR ANALYTICALLY UTILIZING MICROFABRICATED SENSORS DURING WET-UP

TABLE OF CONTENTS

1. FIELD OF THE INVENTION
2. BACKGROUND OF THE INVENTION
   2.1. PREVIOUS DEVICES AND METHODS FOR FLUID ANALYSIS
   2.2. PREVIOUS USES OF POTENTIAL PULSES
3. SUMMARY OF THE INVENTION
4. BRIEF DESCRIPTION OF THE FIGURES
5. DETAILED DESCRIPTION OF THE INVENTION
   5.1. WHOLLY MICROFABRICATED SENSORS
      5.1.1. DISPOSABLE DEVICE FOR SENSORS
   5.2. DATA HANDLING METHODS FOR PERFORMING SIGNAL RESPONSE MEASUREMENTS
      5.2.1. SIGNATURE ANALYSIS
      5.2.2. CALCULATION OF THE SENSOR RESPONSE
   5.3. CALIBRANT FLUID
   5.4. POTENTIOMETRIC SIGNAL RESPONSE
   5.5. AMPEROMETRIC SIGNAL RESPONSE
   5.6. SENSOR ACTIVATION
      5.6.1. METHODS FOR GLUCOSE ACTIVATION
      5.6.2. OPERATIONAL METHODS GENERALLY
      5.6.3. COMPUTATIONAL METHODS FOR ENZYME ASSAYS AND IMMUNOASSAYS
      5.6.4. ADVANCED OPERATIONAL METHODS
   5.7. CONDUCTIVITY MEASUREMENTS
   5.8. SYSTEM INTEGRATION
6. EXAMPLES

CROSS-REFERENCE TO RELATED APPLICATIONS

The present U.S. application is related to prior co-pending U.S. application Ser. Nos. 07/432,714, filed Nov. 7, 1989, and 07/245,102, filed Sep. 15, 1988, the disclosures of which are incorporated by reference herein in their entirety

1. FIELD OF THE INVENTION

The present invention relates to a method of quantifying a preselected analyte species present in fluids, which takes advantage of the well-behaved equilibration wet-up characteristics of dry-stored wholly microfabricated electrochemical sensors. These and other performance characteristics obtain from a manufacturing process, described in the co-pending U.S. application Ser. No. 07/432,714, that attains a high degree of uniformity with regard to the physical dimensions and resulting properties of such electrochemical sensors. The invention allows for the acquisition of analytical data while the signal of the sensor of interest is still undergoing the process of an equilibration wet-up. In particular, the present method includes deriving useful information from microfabricated electrochemical sensors, which sensors had been stored dry, much more quickly than previously thought practical by acquiring and manipulating selected signal measurements well before the sensors have attained a post-equilibrated wet-up state (i.e., steady-state) response. Most notably, the invention provides a method for relating the signal measurements recorded in different fluids to determine the ratio of the concentration of a preselected analyte species in each fluid. The present method utilizes a computational means which is able to distinguish the signal response of a given electrochemical sensor to changes in analyte concentration, which response is fast relative to the slower monotonic "wet-up" behavior of the sensor and its associated reference electrode.

2. BACKGROUND OF THE INVENTION

The recent emphasis in the development of clinical chemistry technology has been directed toward the development of systems for "real time" analysis of biological fluids or those analyses which can be performed in the close proximity of the patient e.g., at the bedside or in the physician's office. Such biological fluids include urine, plasma, serum, and preferably, whole-blood. Clear benefits are achieved if the chemical information required by the physician is obtained during patient consultation and not several hours or days afterward. Although progress has been made toward achieving such a goal, many problems still remain including the limitations of established manufacturing methods to mass-produce electrochemical devices with sufficiently uniform performance characteristics and extended shelf-lives. Of particular interest is the lack of adequate computational techniques which minimize the time required to obtain useful information from such electrochemical devices.

To date, fluid analysis has been carried out using many types of electrochemical sensors in which potentiometric, amperometric or conductimetric measurements are performed in a steady-state or kinetic (e.g., initial rate) mode. Electrochemical sensors employed for these measurements usually consist of a two-component assembly in which a sensitized membrane is interposed between the fluid and an underlying electrode. Some membrane compositions have distinctive species recognition capabilities which enable the electrochemical sensor to detect the analyte of interest specifically and measure its concentration in a complex biological fluid. To date, however, size, complexity and expense limitations, combined with a high incidence of error resulting both from instrument quality control and accidental errors by the operator, have impeded wide spread use of this technology in locations, such as the emergency room and the doctor's office, which are remote from the central clinical chemistry laboratory. Moreover, most analytical test methods currently in use are overly cumbersome or complex. More significantly, the response of the electrochemical device, itself, may be so slow as to make such "real time" analysis very difficult. It should be noted that the concentration of certain components, such as glucose and potassium ion, in a biological fluid (e.g., whole-blood) may change significantly over a prolonged period. The change arises likely from hemolysis of related metabolic processes.

As mentioned previously, a principal obstacle against the successful implementation of "real time" clinical fluid analysis is the lack of reliable sensor manufacturing methods. Equally lacking, however, are data acquisition and manipulation methods which allow the quick retrieval of information from existing chemical sensing devices some of which are stored substantially dry in order to maximize shelf-life. The prevailing standard practice dictates that these "dry-stored" devices be allowed to reach a fully equilibrated "wet-up" state before meaningful sensor data can be recorded.

2.1. PREVIOUS DEVICES AND METHODS FOR FLUID ANALYSIS

Some progress has been made toward the production of improved testing apparatus, including miniaturized chemical sensing devices. U.S. Pat. No. 4,734,184 issued to Burleigh et al. discloses an electrode assembly for monitoring the concentration of a number of gases and ions present in the blood. Although the assembly is stored dry to promote an extended shelf-life, the electrodes, are thoroughly hydrated (wet-up) prior to use. During operation they are in prolonged and equilibrated contact with the many solutions employed, including a calibrant solution, a reference solution and intermittent blood samples. Thus, during the continuous monitoring, for up to 36 hours, of a subject's blood gases, electrolytes and hematocrit levels, all measurements are performed with the sensors providing signal responses in the steady-state. No disclosure is included for deriving meaningful analytical information from solid-state electrodes before the electrodes attain an equilibrated "wet-up" state.

U.S. Pat. No. 4,654,127 issued to Baker and Funk discloses a sensing device equipped with species selective sensors and a rotatable multichamber reservoir in which calibrant and sample solutions are contained but in separate chambers. A plurality of chemical species may be detected by this device. However, as the sensors employed are not microfabricated, only a limited amount of control over the dimensions of the sensors' various components had been possible, resulting in their having nonuniform response behavior and necessitating the batch-wise determination of each sensor's response. The value of the response, e.g., intercept and slope, is then recorded on a bar code which must be read by a table top analyzer before the concentration of the desired chemical species may be calculated. Moreover, the disclosure of this patent is silent on methods for making useful measurements during wet-up of the sensing device. All indications, including those from available product literature, support the supposition that the calibrant and sample solution measurements are carried out after the sensor response has attained a steady-state value. Furthermore, these commercially available sensors are stored in a high humidity package (i.e., substantially wet). This packaging method has the effect of limiting the shelf-life of these sensing devices significantly compared to competitive dry-reagent systems, such as those described below. However, this compromise ensures that the device is substantially "wet-up" at storage and, thus, enables the sensor to provide results fairly rapidly. Unfortunately, this compromise cuts back the device's useful shelf-life quite severely, particularly for enzyme-based sensing devices. Shelf-life, of course, can be extended to some extent by refrigerating the package. However, refrigeration adds to the expense of storage and also means that the device must be allowed to return to room temperature before use.

U.S. Pat. Nos. 4,708,776 and 4,608,149 disclose, on the other hand, improved "dry-operative" ion-selective electrodes. The inventors describe a "dry-operative" electrode as "an ion-selective electrode which provides reproducible potentiometric determination [of] ion activity which is related to the ion concentration of an aqueous test solution with no requirement for wet storage or preconditioning prior to use" (col.2, lines 10–15 of the second patent listed above). These patents also disclose methods of using such electrodes. In particular, the potentiometric determination of the concentration of sodium and potassium ions in an aqueous liquid is described. However, the method relies on a differential measurement which involves contacting the first of two "uniform" electrodes i.e., a pair of identically formed potassium ion-selective electrodes, with the sample liquid and contacting the second electrode with a reference liquid (calibrant) containing a known amount of the ion of interest and then determining the resulting difference between the two potential readings. This method requires that the sample and calibrant solutions be brought into contact with the respective electrodes strictly simultaneously to obtain reliable measurements of the analyte concentrations. Consequently, it is necessary to provide an automated means for the simultaneous application of the calibrant and sample fluids to prevent errors in the measurement.

Pace, in European Patent Application No. 0 012 035, describes self-calibrating miniaturized multiple sensors fabricated on a single chip. The usefulness of this disclosure is quite limited as the exact nature of the materials used for each of the multitude of layers described in the complex sensor structures is not revealed. Pairs of identical electrodes are used, a first member of the pair having at least two distinct electrolyte "layers" of known composition and the other member of the pair either having no electrolyte present in its corresponding layers or having electrolyte present therein at a concentration which is significantly different from the first member. A discussion of the self-calibrating nature of these pairs of matched electrodes is present and makes clear that a differential method of signal measurement is employed to "nullify any drift and offsets in the measurement" (page 23, lines 30–31). Moreover, this reference asserts further that these multiple layers which provide self-calibration "not only assure built-in reliability and accuracy, but relax manufacturing tolerances" (page 26, lines 1–4). Thus, no successful means has been disclosed to manufacture simpler structures with high dimensional tolerances nor has there been any suggestion that useful information may be derived from signal response measurements prior to attaining complete wet-up, much less that a method may be formulated in which such measurements are exploited.

Accordingly, there remains at the present a need for a method which integrates a sensing device, preferably a microfabricated electrochemical sensor, having the requisite predictable, reproducible chemical response and "wet-up" characteristics, and an effective computational technique, which method allows the physician to obtain conveniently precise, accurate determinations of the concentration of analytes of clinical interest. Such determinations are desirably made in five minutes or less, most preferably within about a minute.

2.2. PREVIOUS USES OF POTENTIAL PULSES

Previous workers have utilized potential pulse techniques to increase the sensitivity of the electrochemical measurement or to reduce the flow dependence of the electrode signal. However, these previous applications have always involved fully wet-up devices utilized for the continuous monitoring of analyte concentrations. In such applications, previous workers sought to improve the signal output by taking their readings immediately after the application of a potential pulse across the sensor electrodes. The cathode is open-circuited between the pulses of applied potential. These and related techniques are described more fully in Short, D. L. and Shell, G. S. G. *J. Phys. E.:Sci. Instrum.* 1985, 18, 79–87 and Lilley, M. D. et al. *J. Electroanal. Chem.* 1969, 23, 425–429.

On the other hand, methods exist for activating a catalytic surface including polishing away the surface layer with a fine particle size, inert abrasive material such as alumina or placing the electrode in a corrosive acidic solution such as 1 molar sulfuric acid and cycling the applied potential for several minutes. Clearly, these existing methods are destructive and are inappropriate for the activation of an electrode surface overlaid with microfabricated biolayers.

3. SUMMARY OF THE INVENTION

In accordance with the present invention a method is disclosed for determining the ratio(s) of the concentrations of preselected analyte species in more than one fluid which comprises, in part, providing microfabricated sensors having the requisite characteristics, which will be described more fully below, and performing signal measurements, before the equilibrated wet-up process is complete, while the sensors and reference electrode are in contact with a first fluid and, subsequently and separately, with a second fluid.

In the present method, which fluid is brought into contact with the sensor first is unimportant, so long as a separate signal measurement is made while each fluid is in contact with the sensor and reference electrode. Despite the fact that such measurements are taken before the sensors are fully "wet-up," a process which may take several minutes, useful analytical information about a variety of biological analytes can still, surprisingly, be obtained. The computational techniques for extracting this information from dry-stored microfabricated electrochemical sensors are disclosed. Thus, the present invention allows the simplicity and dry-storage capabilities of microfabricated sensors to be exploited while providing measurements of preselected analyte species as close to "real time" as possible.

It is thus an object of the present invention to provide a method of determining the concentration ratio of a preselected analyte species present in at least two fluids comprising (a) providing at least one microfabricated chemical sensor, which exhibits a response to changes in the concentration of a preselected analyte species, and a reference electrode capable of sustaining a well-behaved reference potential for a period of time sufficient to permit the completion of at least two signal measurements, against which reference potential of said sensor is measured, which sensor and reference electrode have been stored substantially dry, and which response is sufficiently rapid or "fast" relative to the "slow" monotonic wet-up behavior exhibited by said sensor and reference electrode when contacted with fluid; (b) establishing electrical contact between said sensor, reference electrode and external computational means; (c) contacting said sensor and reference electrode with a first fluid; (d) performing the first of said signal measurements in a preselected first time window in the presence of said first fluid; (e) displacing said first fluid; (f) contacting said sensor and reference electrode with a second fluid; (g) performing the second of said signal measurements in a preselected second time window in the presence of said second fluid; and (h) relating said first and second signal measurements to the known concentration of said analyte species in one of said first or second fluids, to determine the unknown concentration of said analyte species in the other of said fluids before said sensor attains full equilibrated wet-up.

It is also an object of the present invention to provide a method of determining the concentration of a plurality of preselected analyte species present in a sample fluid comprising, as a first step, providing an array of microfabricated potentiometric and amperometric sensors, each sensitive to changes in the concentration of a particular preselected analyte species, and which array also comprises one or more reference electrode capable of sustaining a well-behaved reference potential for a sufficient period of time. Preferably, one reference electrode is dedicated to said potentiometric sensors and another reference electrode is dedicated to said amperometric sensors. However, a single reference electrode may also be used for both types of sensors, if said amperometric sensors are also supplied with a common counter electrode. The counter electrode is designed to prevent polarization of the reference electrode, the effect of which polarization is more deleterious to the performance of potentiometric sensors. As noted, above, each sensor has been stored substantially dry and exhibits a response to said changes in the concentration of said particular preselected analyte species which is sufficiently rapid relative to the monotonic wet-up behavior of said sensors. After providing an array of such sensors, the subsequent steps of the present invention include: (b) establishing electrical contact between said array of sensors and external computational means; (c) contacting said array of sensors with a first (e.g., calibrant) fluid; (d) performing a first set of signal measurements in a preselected first time window in the presence of said first fluid; (e) displacing said first fluid; (f) contacting the array with a second (e.g., sample) fluid suspected of containing said plurality of analyte species, such that said array of sensors is in contact with said second fluid; (g) performing a second set of signal measurements in a preselected second time window in the presence of said second fluid; and (h) relating said first and second sets of signal response measurements to determine the concentration of a plurality of said preselected analyte species in said second fluid, based on the known concentrations of each of said preselected analyte species in said first fluid.

It is a further object of the present invention to provide a method for activating the electrode surface of an amperometric sensor by subjecting the sensor to a series of potential changes while it is in contact with a fluid, preferably a calibrant fluid.

Yet another object of the present invention involves providing a conductivity sensor by which the conductivity of the fluid in contact with the conductivity sensor may be determined and related, if desired, to the hematocrit level in the sample, or more simply to provide an indication of whether the fluid is calibrant, plasma, serum or whole-blood, or even to provide a check on the presence of a sample of calibrant fluid.

Still another object of the present invention includes a determination of the concentration of the analyte species of interest in about one minute using dry-stored sensors.

Yet another object of the present invention relates to minimizing the incidence of a test "failures" by incorporating data collection methods which allow the testing apparatus to scrutinize the integrity of the acquired signals and to manipulate the data set to exclude extraneous or aberrant data points which may otherwise lead to a rejection of a particular analysis.

Other objects of the present invention should be readily apparent to those skilled in the art from the preceding discussion, as well as the following additional detailed disclosure.

4. BRIEF DESCRIPTION OF THE FIGURES

FIG. 1 illustrates the raw waveform exhibited by a microfabricated potentiometric potassium ion sensor on grounding (a), exposure to a calibrant fluid (b), initial sensor wet-up (c), followed by transition to a sample fluid (e). Suitable preselected time windows for data acquisition in each fluid are indicated by variable time segments (d), for the first fluid, and (f), for the second fluid.

FIG. 5b illustrates the response to a fluid change of the activated glucose sensor of FIG. 4a.

5. DETAILED DESCRIPTION OF THE INVENTION

Figure 2A:
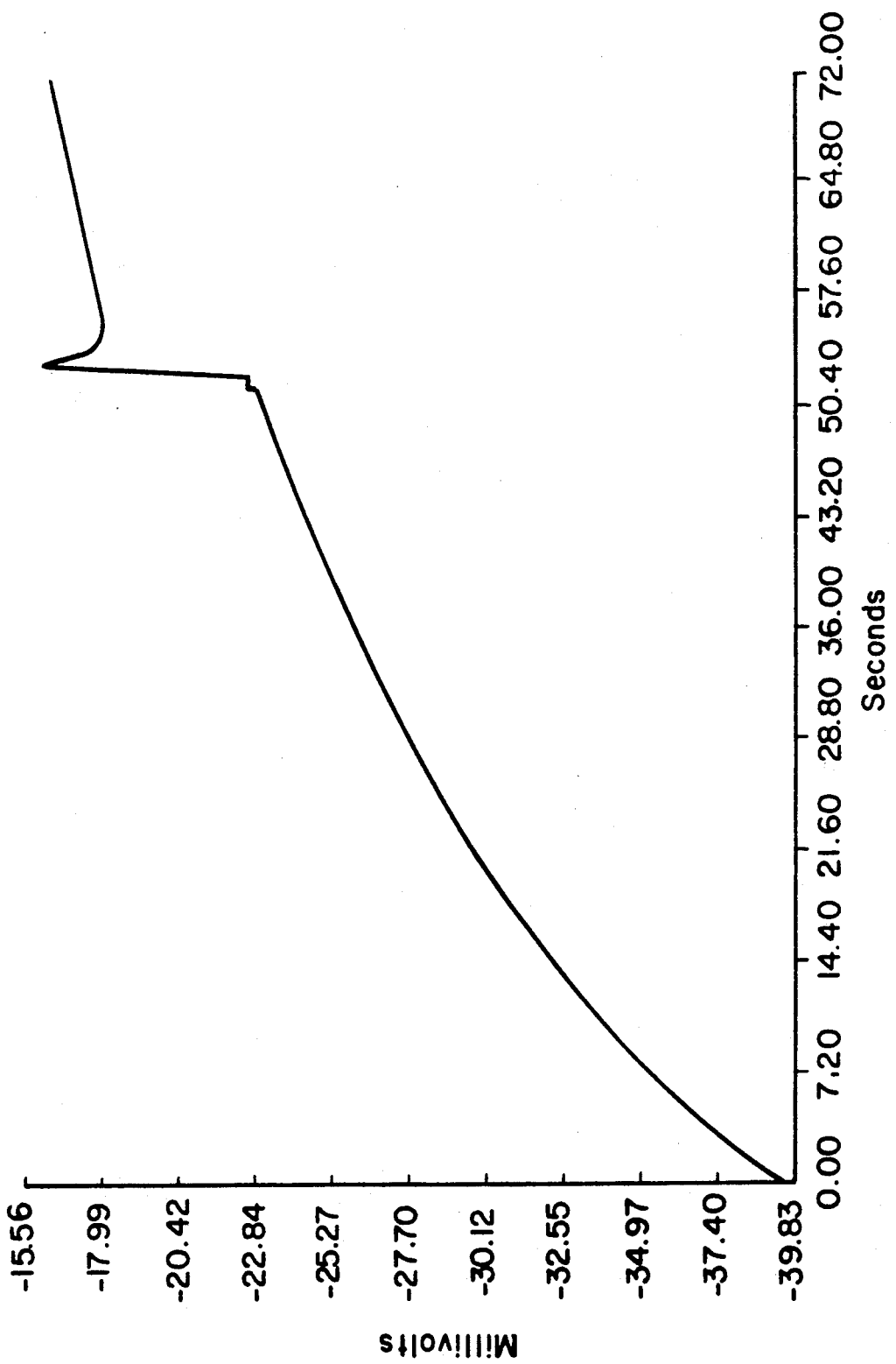
FIGS. 2a-2e show the response to a fluid change of a potassium ion sensor, sodium ion sensor, chloride ion sensor, urea sensor and microfabricated on-board reference electrode, respectively, with respect to an external standard Corning reference electrode.
Figure 2B:
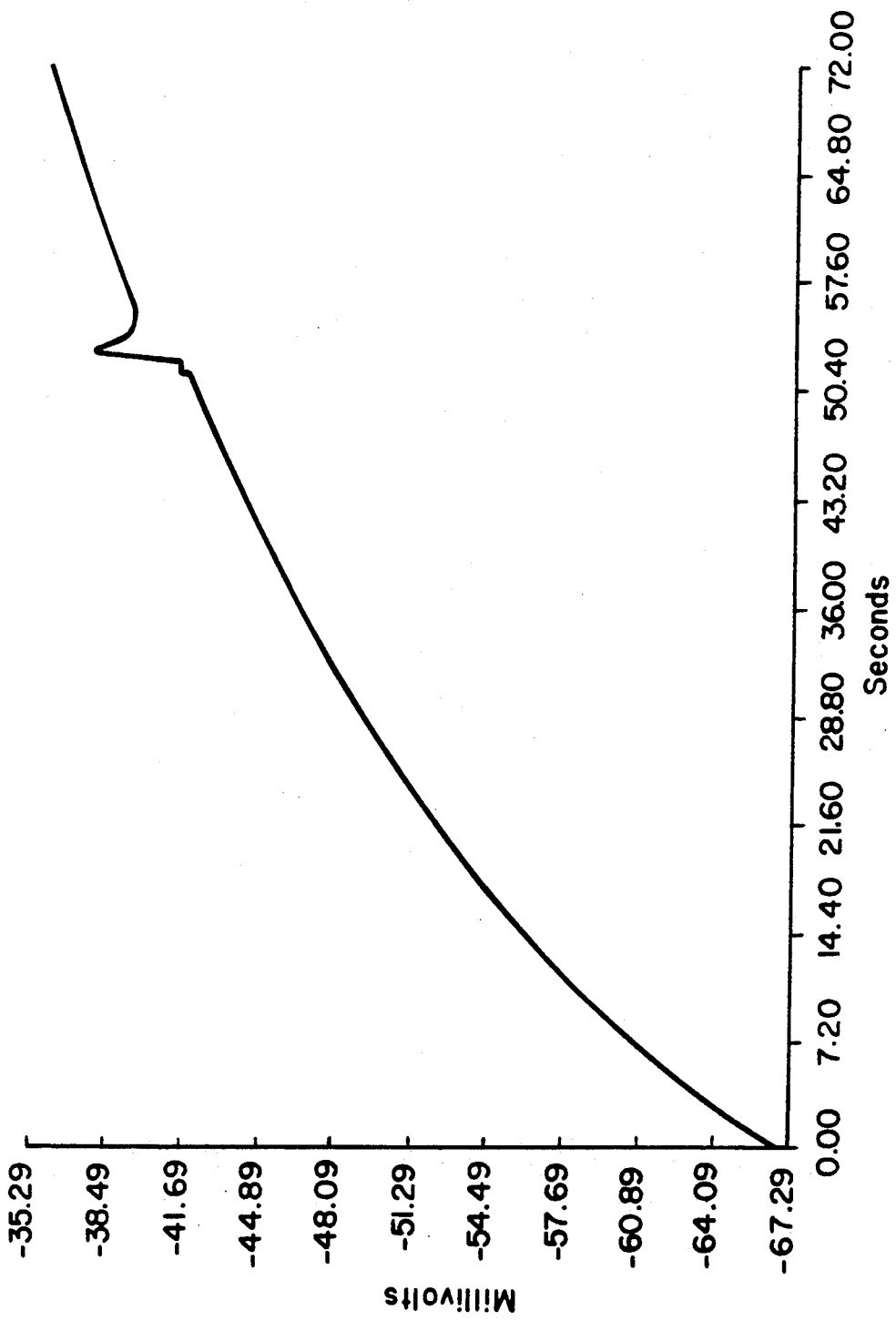
Figure 2C:
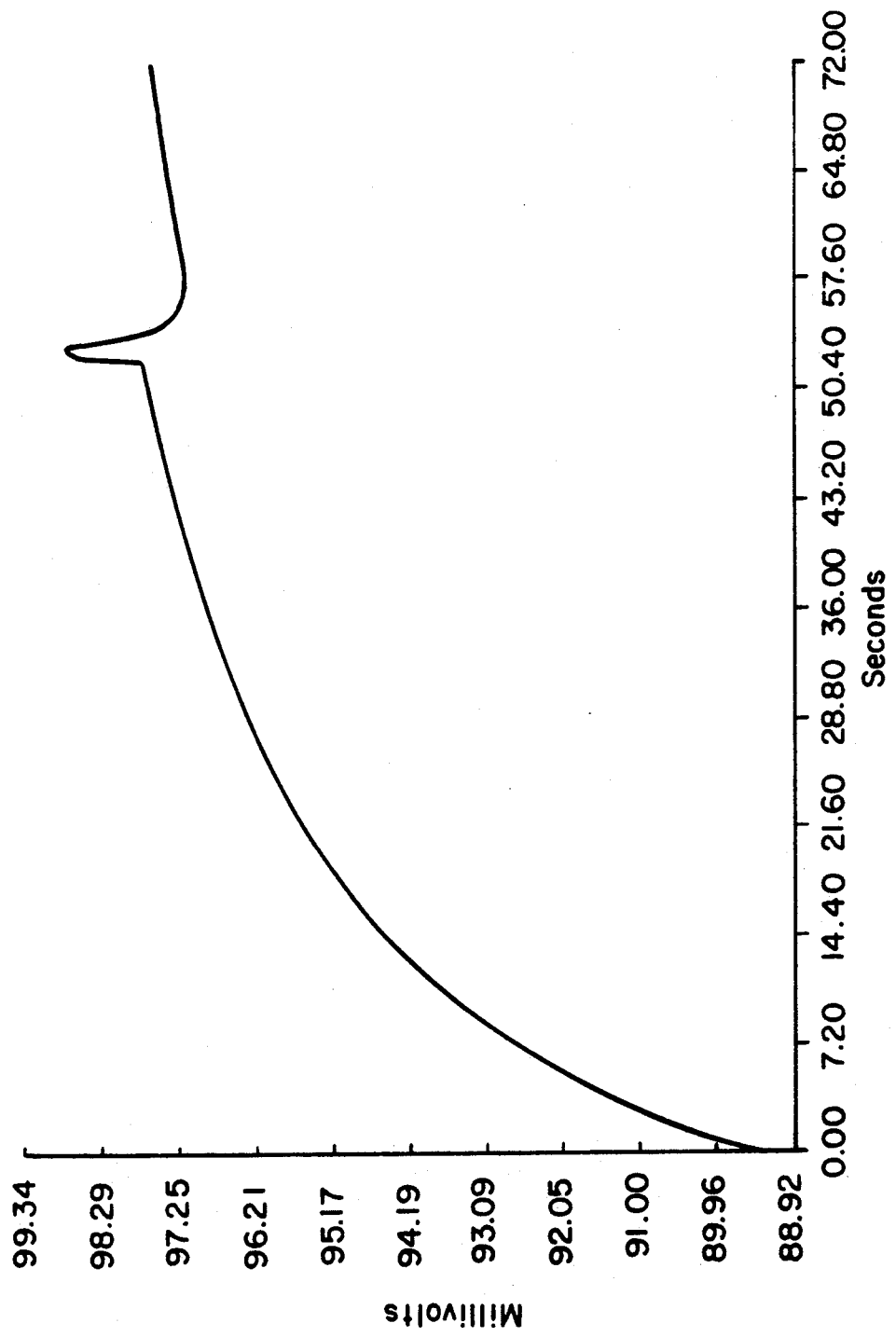
Figure 2D:
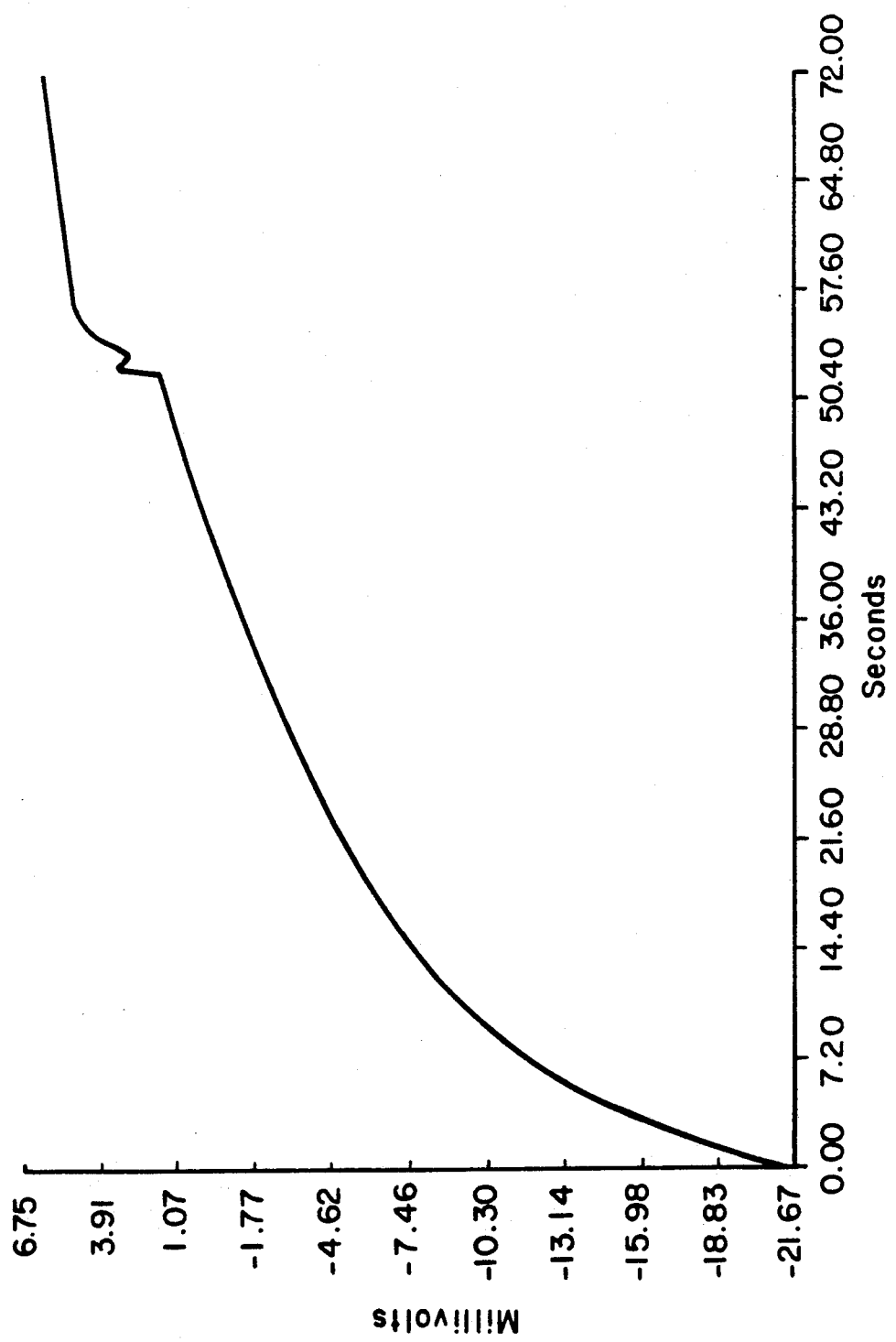
Figure 2E:
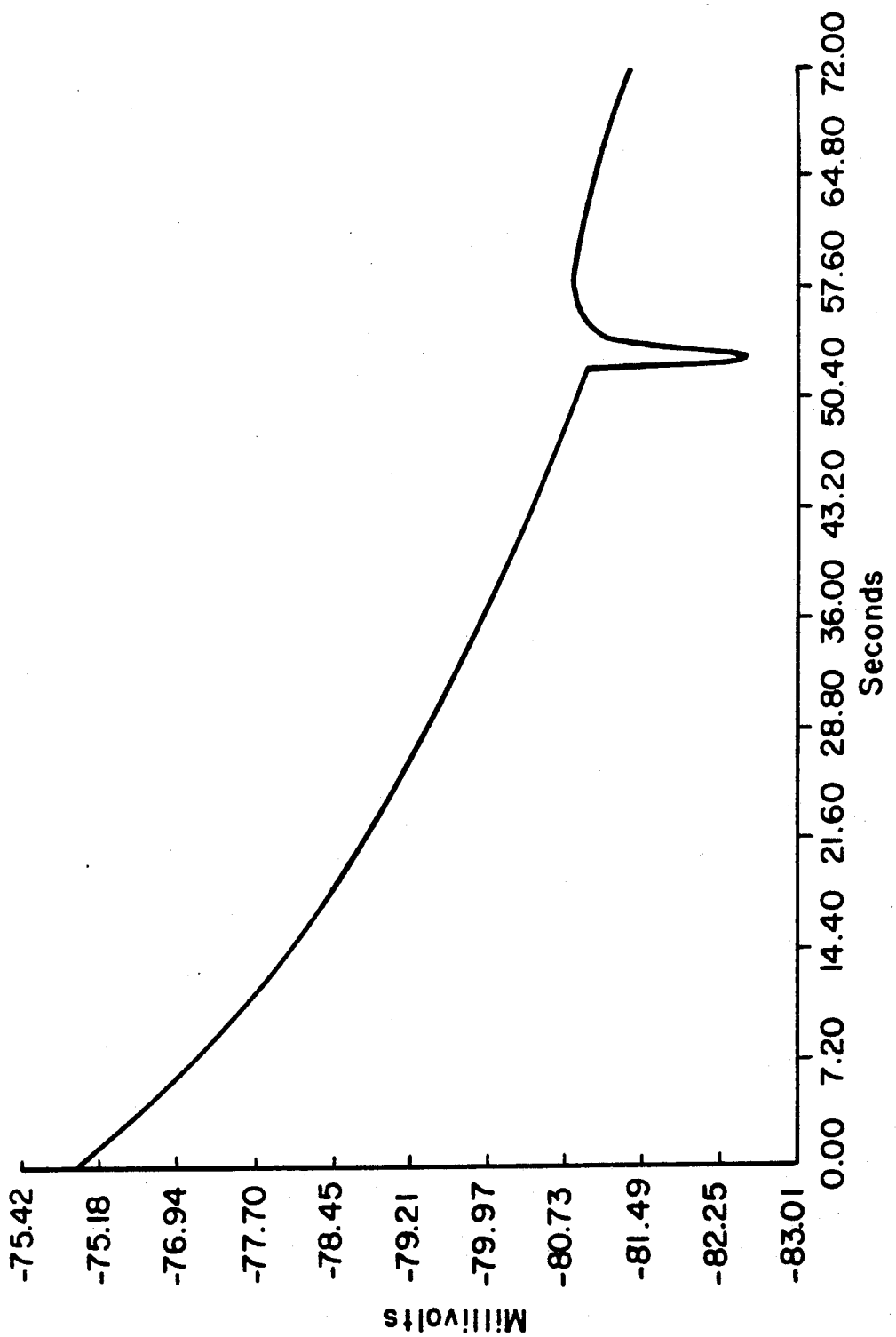
Figure 3A:
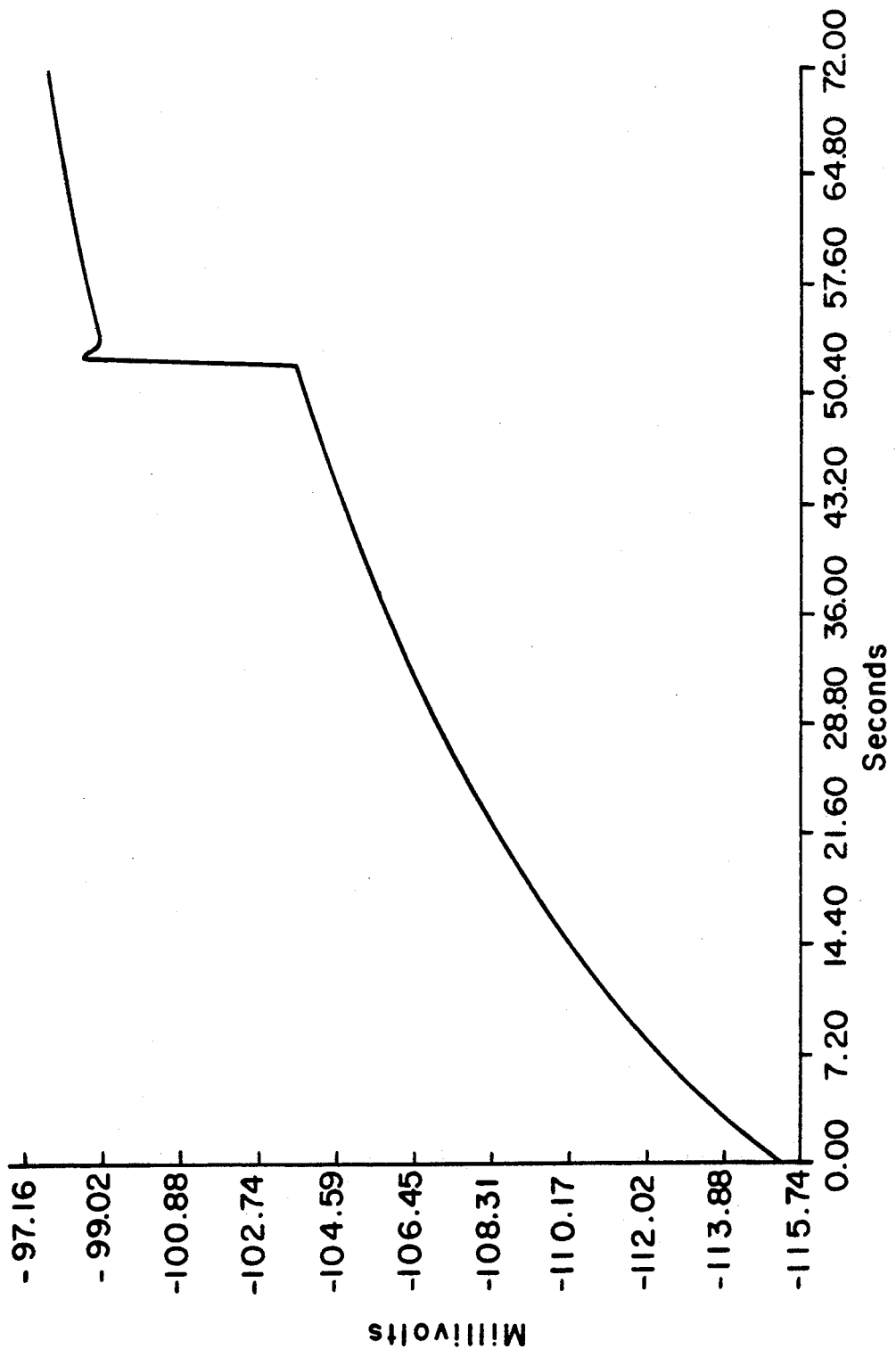
FIGS. 3a-3d show the response to a fluid change of a potassium ion, sodium ion, chloride ion and urea sensors, respectively, with respect to a microfabricated on-board reference electrode.
Figure 3B:
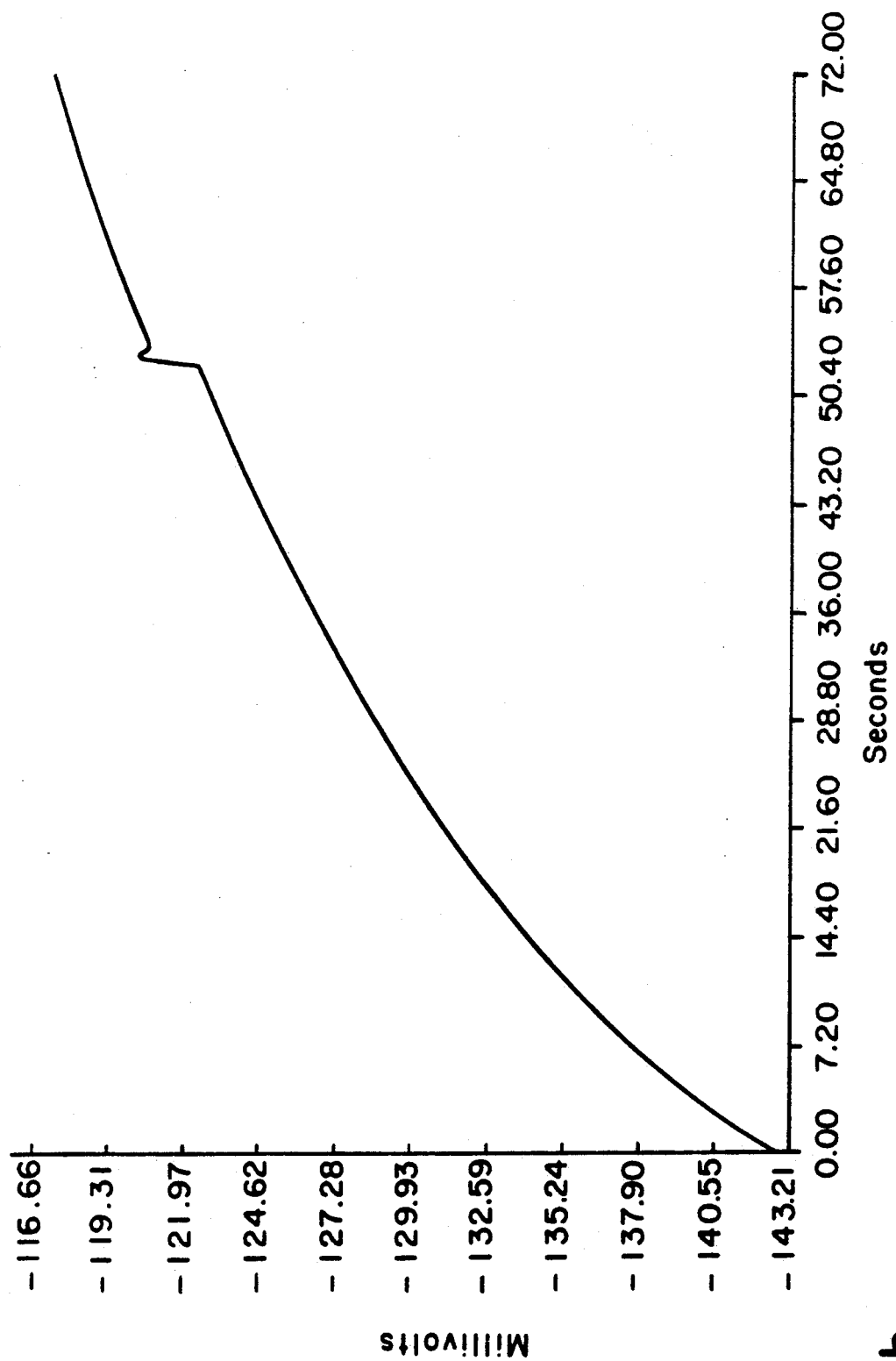
Figure 3C:
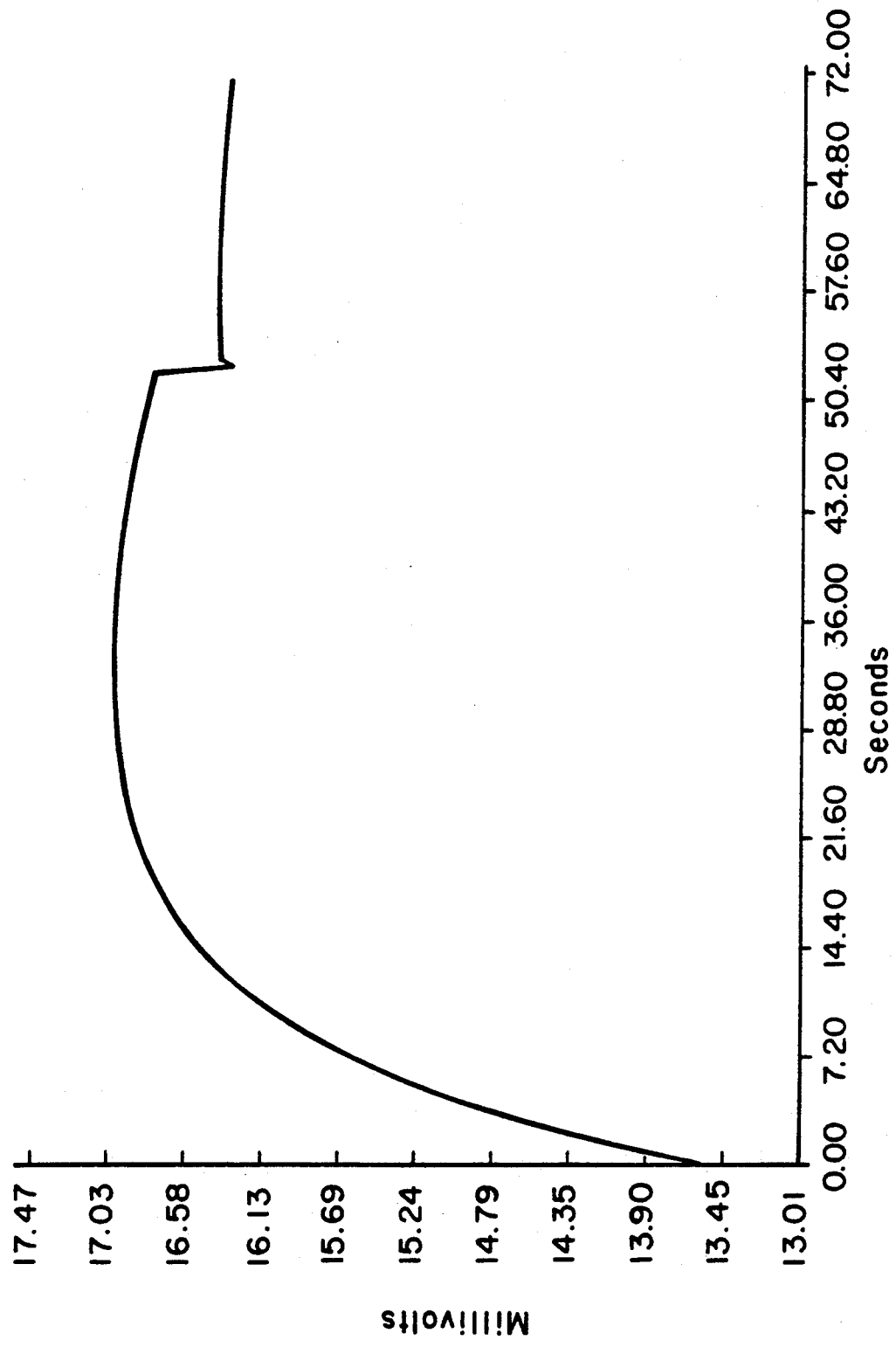
Figure 3D:
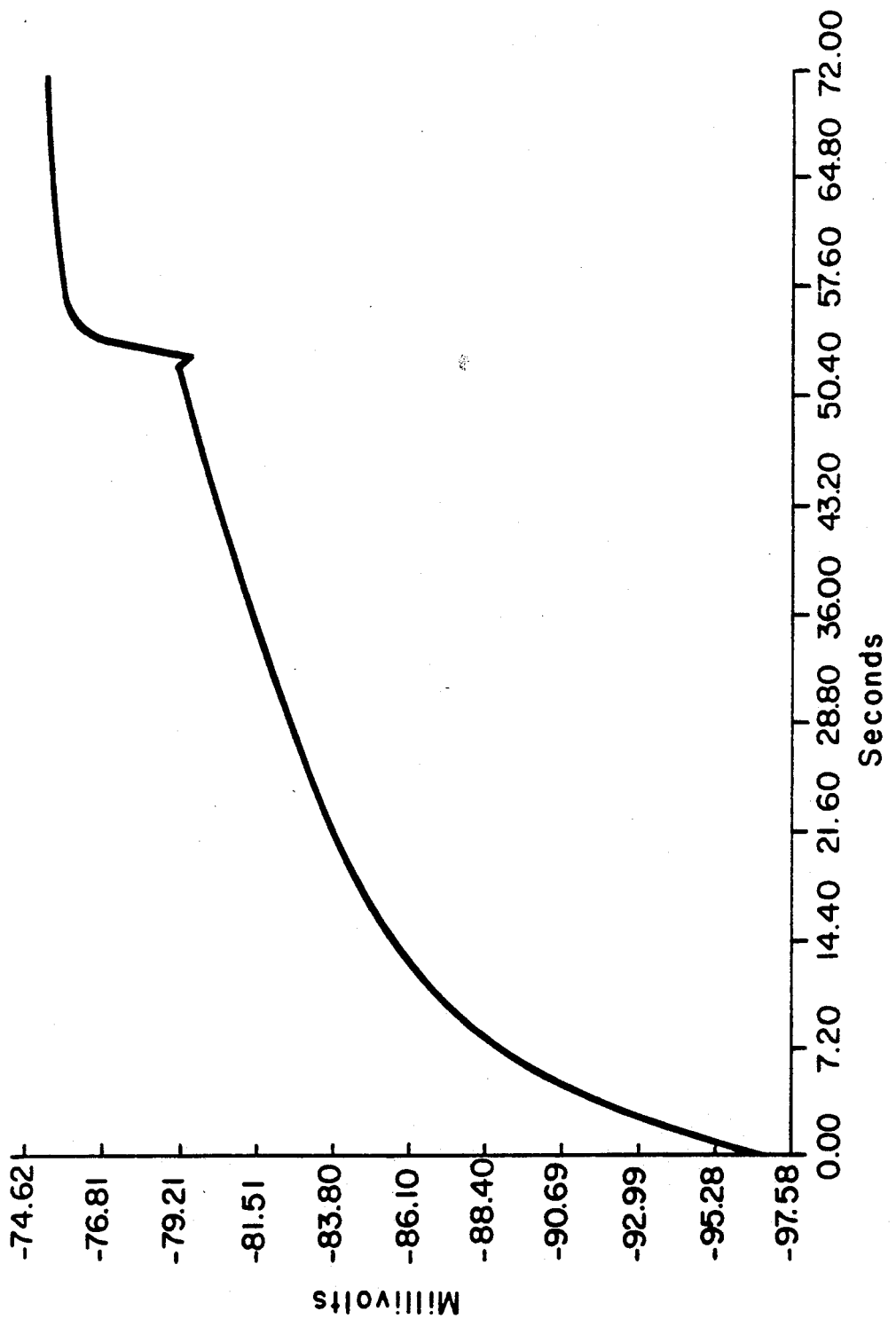

The method of the present invention seeks to integrate the quantifiable, predictable behavior of microfabricated sensors during the equilibrated wet-up process with computational techniques, including data handling or collection methods, which may be implemented by the testing apparatus or external computational means, to arrive at a close estimate of the concentration of an analyte of interest in a given sample fluid.

The "equilibrated wet-up" process is the means by which dry-stored sensors, by exposure to a fluid comprised of an aqueous medium, wet gas and the like, reach an operational state and, eventually, a steady-state. Here, the term "equilibrated wet-up" is used to encompass, not only ingress of water through the various membrane layers to the electrode surface, but also all of the physicochemical changes that occur prior to a sensor attaining that steady-state response. These changes and their consequences include: the hydration of each membrane layer and its effect upon migration therethrough of analytes, cofactors, ionophores, enzyme, affinity-labels, and the like; the hydration of the enzyme-containing layer and its effect on the activity of enzymes or the selectivity of ionophores and affinity labels (i.e., the effect on their binding coefficients); the hydration of the electrode surface and the responsiveness of the sensor which may be a function, for example, of the relative surface populations of metal oxide and metal hydroxide sites, or, alternatively, the degree of ligand-ligand substitution in which a silver-silver halide surface may be transformed into a halo-aquo metal complex. All of such changes that occur, before a fully wet-up, equilibrated sensor is obtained, can give rise either singularly or in concert, to a monotonically changing signal output despite the fact that the physical and chemical properties of the fluid, which may be comprised of an aqueous liquid or a wet gas, in contact with the sensor are not changing (i.e., the concentration of the preselected analyte in the fluid remains constant, along with the temperature, pH, osmotic pressure, ionic strength, etc., of the fluid, especially the calibrant fluid).

The processes described above may be considered passive in the sense that upon contact with fluid they occur spontaneously. However, the electrode surface of an amperometric sensor presents a special case in that its redox properties are substantially affected by the voltages that have been applied to it previously. In this sense, electrochemical activation of the electrode surface by applying a sequence of difference voltages can contribute significantly to the reduction of the time it takes before the sensor operates reliably in a steady-state manner, and therefore, contributes significantly to the apparent "wet-up" (or RC wet-up) of the sensor.

The monotonic wet-up signal is usually described by a resistance capacitance (RC) time-constant because it can be simulated electronically by connecting a resistor and capacitor either in series or in parallel. Thus, for a potential step applied to such a circuit, an exponentially decaying current is obtained with a time-constant, $\tau = RC$ where the current, $i = E/Re - (t/\tau)$. In this example the current necessary for changing the capacitor drops to 37% of its original value at $t = \tau$ and to 5% of its original value at $t = 3\tau$. This latter value is often referred to as the 95% response-time. For the sensors described here useful analytical information is obtained well before the sensors have transformed from the dry-state to a hydrated or wet-up state in which the sensors provide a signal which is 95% of the expected equilibrated steady-state value.

A good introductory discussion of this RC concept can be found in Lindner, E. et al. "Dynamic Characteristics of Ion-Selective Electrodes," CRC Press, 1988 and the references cited therein, the complete disclosures of which are incorporated herein by reference. It should be noted that while the exponential model for time evaluation of the chemical sensor signal is usually referred to as an "RC time-constant," no special detailed elucidation or assumptions about chemical or physical capacitive or resistive elements of the sensor's operation are required to verify the applicability of the exponential model.

In the present invention, it has been surprisingly discovered that the RC time-constant for wet-up associated with the present wholly microfabricated sensors and reference electrodes can be manipulated and modeled closely. The reproducibility and predictability of this, wet-up RC time-constant is, in turn, a product of the microfabrication techniques described in the following section, and more fully in related co-pending U.S. application Ser. Nos. 07/432,714 and 07/245,102. Such microfabrication techniques provide much finer control over the dimensions of overlaid layers than can be achieved by previous techniques, including lamination. Indeed, a multiplicity of electrochemical sensors can now be fabricated on a single silicon wafer. These electrochemical sensors, including the first practical microfabricated reference electrode, possess sufficiently well-behaved properties to allow electrochemical measurements to be made with the precision and accuracy required in clinical chemistry.

As will be described in more detail, below, the present inventors have discovered that the time evolution or rate of change in the monotonic wet-up signal can be predicted to a high degree of accuracy at any time after initial contact of the sensor and reference electrode with a fluid. This ability to model, analyze and manipulate the RC time-constant is an important aspect of the present method which allows the concentration of an analyte species of interest to be determined quickly and reliably before the sensors have attained a fully wet-up, equilibrated state.

An equally important element of the present invention and one which is a direct consequence of having a reproducible, predictable wet-up RC constant is that the RC constant associated with the sensor's response to changes in the concentration of a preselected analyte is also highly predictable and precise.

The RC time-constant, $\Omega F$, is in units of seconds (sec) as evident from the following relationships:

$R$ (resistance) $= \Omega.\text{ohms} = V/i$ $C$ (capacitance in F, Faraday) $= q/V = (i \times \text{sec})/V$ since, $RC = \Omega F$, then $RC = (V/i) \times (i \times \text{sec})/V = \text{sec}$ When a chemical sensor undergoes a change in its signal in response to a change in the analyte concentration, the exponential time constant governing the time dependence of the signal of a chemical sensor varies as $\tau \alpha L^2/D$. (See, Lindner, E. et al., above, "Dynamic Characteristics of Ion-Selective Electrodes", DRC Press, 1988 and earlier work by Buck, R. P. cited therein, especially Chapter 1 of "Ion-Selective Electrodes in Analytical Chemistry", Freiser, H., (Ed), Plenum Press, 1978).

The time taken by a sensor to attain the steady-state response to a change in concentration of an analyte can be described by an RC time-constant. Thus, the $RC_{response}$ time can be approximated by the relationship, $RC = L^2/D$ where, L is the thickness of the membrane layer in cm and D is the diffusion coefficient in $cm^2 sec^{-1}$ of the analyte through the membrane. The diffusion coefficient for glucose through a membrane layer is typically about 100 times less than its diffusion coefficient in solution ($D_{soln} = 10^{-6}$ cm$^2$ sec$^{-1}$, $D_{memb} \approx 10^{-8}$ cm$^2$ sec$^{-1}$). Thus, if the membrane layer is about 1 $\mu$m ($10^{-4}$ cm) in thickness, then $RC_{response}$ time is approximated to be $(10^{-4})^2/10^{-8}$ or ca. 1 sec. The $RC_{wet-up}$, whose magnitude is on the order of tens of seconds, is thus "slow" relative to the response time. For example, the wet-up time-constants for the sensors shown in the Figures (e.g., FIGS. 1–3) exhibit $\tau$ values of ca. 20 sec. As described below, when the wet-up process proceeds to an incomplete level where $\tau < t = 3\tau$ i.e., the rate of change in the signal is sufficiently small, it is possible to model this rate as a linear drift rate (See, Table 1).

Clearly, the time required for a diffusion front of an analyte species to penetrate a membrane layer and establish a steady-state response increases with increasing membrane thickness. Thus, having a manufacturing method which attains a high degree of dimensional control over sensors' overlaid structures is crucial to obtaining devices with predictable, reproducible wet-up and response time behavior.

In addition to describing a method involving a single sensor, the present invention is also concerned with the effective operation of an array of sensors each sensitive to a particular preselected analyte species. Each sensor in the array may be operating in one of a number of possible modes including, but not limited to, those designed to perform standard potentiometric, amperometric and conductimetric measurements or kinetic measurements based thereon. The concurrent operation of an array of different electrochemical sensors composed of some, or all, of these types, presents its own unique set of problems.

Moreover, certain types of microelectrode assemblies are susceptible to inactivation, or a loss of surface catalytic activity, and require reactivation to secure the highest level of sensitivity.

The following is a detail description of each element of the present analytical method for deriving the concentration of at least one, preferably a number, of preselected analyte species.

5.1. WHOLLY MICROFABRICATED SENSORS

Wholly microfabricated sensors, the availability of which comprises a preferred element of the present method, are described in detail in the applicants' prior co-pending U.S. application Ser. No. 07/432,714. Additional aspects related to the manufacture of integrated ambient sensing devices, including a microfabricated reference electrode, are described in U.S. Pat. No. 4,739,380 and prior co-pending U.S. application Ser. No. 07/156,262, the complete disclosures of which are incorporated herein by reference. These microfabricated sensors are manufactured in such a way as to avoid the errors and non-uniformity introduced by manual deposition of membranes and the like at various stages of the manufacturing process. Thus, a combination of thin film techniques, including wafer-level photolithography and automated microdispensing, are used to produce hundreds of identical sensors, or an array of different sensors, on a single silicon wafer. Reference electrodes made by the same process are also established in a highly controlled fashion.

Such a reference electrode is necessary for electrochemical measurement of chemical or biochemical species in a sample solution (See, Ives, D. V. G. and Janz, G. J. "Reference Electrodes, Theory and Practice," Academic Press, 1961, the complete disclosure of which is incorporated herein by reference). In the case of potentiometric measurement, the signal measured is the potential of a chemically responsive electrode (sensor) with respect to the potential of the reference electrode. Ideally, the potential of the reference electrode is strictly independent of the chemical composition of the solution that it contacts. A reference electrode is also necessary for an amperometric measurement because it controls the potential of the amperometric sensor. Because such a high degree of control is present with regard to the composition of these layers, their physical dimensions, as well as their location on the sensor array, the characteristics and specification of each sensor on the wafer, or any similarly produced wafer, are well-behaved and predictable.

In particular, the microfabricated sensor and reference electrode which are most preferred comprises a permselective layer, superimposed over at least a portion of said sensor, having a thickness sufficient to exclude substantially molecules with a molecular weight of about 120 or more while allowing the free permeation of molecules with a molecular weight of about 50 or less; and a biolayer superimposed over at least a portion of said permselective layer and said sensor, which biolayer comprises (i) a sufficient amount of a bioactive molecule capable of selectively interacting with a particular analyte species, and (ii) a support matrix in which said bioactive molecule is incorporated, which matrix is derived from the group consisting of a photoformable proteinaceous mixture, a film-forming latex, and combinations thereof and through which matrix said analyte species may freely permeate and interact with said bioactive molecule.

In a preferred embodiment of the present invention the permselective layer is derived from a polymer film, most preferably comprising a heat-treated film of a silane compound having the formula $R'_nSi(OR)_{4-n}$, in which n is an integer selected from the group consisting of 0, 1, and 2; R' is a hydrocarbon radical comprising 3-12 carbon atoms; and R is a hydrogen radical or a lower alkyl radical comprising 1-4 carbon atoms.

The bioactive molecule of the sensor biolayer may be selected from a wide variety of molecules well known to those skilled in the art and may include, for example, an ionophore, an enzyme, a protein, polypeptide, nucleic acid or an immunoreactive molecule. Typically, the bioactive molecule is an ionophore or an enzyme.

In another preferred embodiment of the microfabricated sensor, the photoformable proteinaceous mixture comprises (i) a proteinaceous substance; (ii) an effective amount of a photosensitizer uniformly dispersed in said proteinaceous substance; and (iii) water. Examples of proteinaceous substances which are useful in the present invention include albumin, casein, gamma-globulin, collagen, derivatives, and mixtures thereof. The most preferred proteinaceous substance is an animal gelatin, especially fish gelatin. Many types of photosensitizers abound. Of particular interest, however, are high oxidation state transition metal compounds, especially iron and chromium salts.

The film-forming latex may comprise an aqueous emulsion of a polymer or copolymer derived from synthetic or natural sources.

Of course, additional layers may be present in the microfabricated sensors. For example, additional layers may be used to attenuate the transport of selected molecules, including analyte species, through the sensor. An electrolyte layer may be present especially for the potentiometric sensors or the reference electrode structure. A more complete description of the reference electrode structure may be found in applicants' prior co-pending U.S. application Nos. 07/432,714 and 07/156,262.

It should be re-emphasized that an array of sensors may use a common reference electrode. Thus, a series of potentiometric sensors may be assembled for measuring the activity of several electrolytes concurrently, the signal of each sensor being determined relative to the potential of the common reference electrode. Amperometric sensors may have a slightly different configuration, each comprising a sensor and a counter electrode, for example, but with all the sensors in an array sharing a common reference electrode.

The conductivity sensor for a hematocrit measurement is plain in design comprising two noble metal electrodes spaced at an appropriate distance on the proposed array. In carrying out a conductivity measurement, an electric field is generated between the pair of metal electrodes by applying an a.c. signal (a d.c. signal may also be employed). Preferably, the effect of the field is limited predominantly to the fluid compartment directly above the pair of metal electrodes. This configuration maximizes the device's sensitivity toward erythrocytes. It should be noted that several factors need to be taken into account in selecting the appropriate frequency for the a.c. signal. These factors include minimizing Faradaic processes at the electrode surface while maximizing the distortion of the field by the erythrocytes.

The electrochemical sensors which are perhaps the most complex, in terms of the need for additional reagents, are those sensors used to perform kinetic measurements. These types of sensors are useful in determining, for instance, the activity of an enzyme as reflected by the rate of change in the concentration of a detectable species consumed or produced by the enzyme-linked reaction. Hence, the activity of a particular enzyme in a given sample may be established. Also, certain enzyme-linked immunoassays may be carried out, paving the way for the analysis of a wide variety of immunoreactive and affinity-active species, including antigens, haptens, antibodies, viruses and the like.

Thus, a preferred embodiment of a sensor intended for enzyme or immunoassays should have a layer, accessible to the sample fluid, to which is immobilized one or the other of a ligand/ligand receptor pair. Again, the reader is referred to the disclosure of applicants' prior co-pending U.S. application Ser. No. 07/432,714 for further details.

5.1.1. DISPOSABLE DEVICE FOR SENSORS

The microfabricated sensors described above are preferably contained in a disposable device which can be adapted for performing a variety of measurements on blood or other fluids. The disposable device is constructed to serve a multiplicity of functions including sample collection and retention, sensor calibration and measurement. During operation, the disposable device may be inserted into a hand-held reader which provides the electrical connections to the sensors and automatically controls the measurement sequence without operator intervention.

A suitable disposable device includes upper and lower housing members in which are mounted a plurality of sensors and electrical contacts and a pouch containing a calibrant fluid. The sensors generate electric potentials based on the concentration of specific ionic species in the fluid sample tested. A double sided adhesive sheet is situated between the upper and lower housing members to bond the housing members together and to define and seal several cavities and conduits in the device.

A first cavity is located at the center of the device having a pin at the bottom of the cavity and a hinged disc at the top of cavity. A sealed pouch containing calibrant fluid resides in the cavity and a first conduit leads from this cavity toward the sensors. A second conduit has orifice at one end for the receipt of a fluid sample while the other end of the tube terminates at a capillary break. A third conduit leads from the capillary break across the sensors to a second cavity which serves as a sink. The first conduit joins the third conduit after the capillary break and before the sensors. A third cavity functions as an air bladder. When the air bladder is depressed, the air is forced down a fourth conduit into the second conduit.

In operation, a fluid sample is drawn into the second conduit by capillary action by putting the orifice at one end of the conduit in contact with the sample. After the sample fills the second conduit, the orifice is sealed off. The pouch containing the calibrant fluid is then pierced by depressing the disc down on the pouch which causes the pin to pierce the other side of the pouch. Once the pouch is pierced, the calibrant fluid flows from the cavity through the first conduit to the third conduit and across the sensors at which time the sensor calibration is performed. Next, the air bladder is depressed forcing air down the fourth conduit to one end of the second conduit which forces the sample out the other end of the conduit, past the capillary break, and into the third conduit and across the sensors where measurements are performed. As this is done, the calibration fluid is forced out the third conduit into the second cavity where it is held. Once the measurements are made, the disposable device can be discarded.

The hand-held reader includes an opening in which the disposable device is received, and a series of ramps which control the test sequence and the flow of the fluid across the sensors. As the disposable device is inserted into the reader, the reader ruptures the pouch of calibrant fluid by depressing the hinged disc. The reader then engages the electrical contacts on the disposable device, calibrates the sensors, depresses the air bladder to force the fluid sample across the sensors, records and electric potentials produced by the sensors, calculates the concentration of the chemical species tested and displays the information for use in medical evaluation and diagnosis.

Thus, for example, to measure the potassium concentration of a patient's blood, the physician or technician pricks the patient's finger to draw a small amount of blood. The physician then puts the orifice of the device into the blood, drawing the blood into the device through capillary action. The physician then seals off the orifice and inserts the device into the reader. Upon insertion, a sequence of events is automatically initiated by the reader without intervention from the physician. The reader automatically causes the calibrant pouch to be punctured so that the calibrant fluid flows over the sensors, activating the sensors and providing the necessary fluid for calibration. The electrical contacts of the device are then automatically connected to the reader and the calibration measurements are automatically made. The reader then automatically depresses the air bladder in the disposable device causing the sample to flow over the sensors. The electric potentials generated by the sensors are read and the concentration of the chemical species is automatically calculated. The result is displayed or output to a printer for the physician to utilize.

Upon completion of the process, the physician removes the device from the reader and disposes of it properly. The reader is then ready to perform another measurement which is initiated by the insertion of another disposable device.

5.2. DATA HANDLING METHODS FOR PERFORMING SIGNAL RESPONSE MEASUREMENTS

The present data handling methods allow the instrument housing the external computational, data storage and display means to extract the needed information (i.e., the electrochemical response of each sensor in the array) from a background which includes sensor wet-up, fluidics transients (those transients associated with fluid flow) electronic noise, contact noise associated with the electrode outputs and the computation means and other intermittent artifacts or signal fluctuations. The reader is referred to applicants' prior co-pending U.S. application Ser. No. 07/187,665 for further information concerning salient components of a hand-held instrument which may be used for processing the sensors signals.

The data handling techniques include computational methods which are designed to relate the first and second signal measurement and, thus, provides the concentration ratios of the preselected analyte species in the first and second fluids. These computational methods distinguish the relatively fast response of the sensor (either potentiometric or amperometric) to concentration changes from the slower monotonic wet-up of both the sensors and reference electrode. After studying the particular embodiments described herein, it should be apparent to one skilled in the art, however, that more sophisticated computational methods may be employed to process signals, should non-monotonic wet-up behavior be encountered. Still other types of computational methods may hereafter be conceived for detecting signal defects as discussed below. In any event, a first order approximation can be extended to a more general nth order polynomial relationship, exponential relationship and the like, if the need is apparent. The only concern with higher order computations is their suitability for extrapolation.

Hence, in one embodiment of the present method a computational method is employed to detect unusable signals caused by: changes in the nature of the fluid in contact with the sensor, electrical noise from the contacts or connections between the individual sensors and the external computational means, as well as other extraneous intermittent artifacts. The present computational methods may be used to provide an indication of the occurrence of artifacts which combine to give an unacceptable measurement cycle. In a preferred embodiment of the present method, the standard computational method is extended to allow the instrument to remove the offending artifacts or aberrant data point from the acquired data set. The "corrected" subset is then processed in the same way to provide a useful measurement. Thus, certain but not all analysis, which otherwise would have been discarded as "failures," are salvaged under appropriate conditions.

It should be pointed out that the computational methods employed in the present method, though similar to known signal processing methods, perform, inter alia, a non-trivial assessment of how the electrochemical response of interest and the wet-up behavior or artifacts contribute to the raw waveforms. The desired signals must then be derived or further manipulated before useful information is obtained.

The present data handling method can be broken down into two main parts comprising a data acquisition portion and another for data manipulation and analysis. Each portion has its own set of computational methods, and their relationship may be better understood by referring to FIG. 7, below.

During the data acquisition portion of the data handling method, the analog signals obtained from the sensors are converted into a digital format for recording in the data memory. The electronics are designed to be appropriate for high impedance potentiometric sensors with sufficient resolution over the expected range of voltage measurements. The electronics for the amperometric sensors, which measure current, include current to voltage converters and are also designed to have sufficient resolution over the expected range of current measurements. During the measurements, the fluid is grounded so as to prevent the fluid potential from floating out of the range of the operational amplifiers.

It should be pointed out that the amperometric sensors are preferably subjected to an electrochemical activation process. Applicants speculate that this activation process enhances the catalytic activity of the sensor electrode surface toward reduction or oxidation of certain redox active chemical species. Further discussion on this electrical activation process is presented in a later section, below.

Also, this portion of the data handling method includes the collection and digital storage of conductivity measurements. As mentioned elsewhere in this disclosure, these conductivity measurements are related to the analysis of the patient's hematocrit levels and, also, system quality assurance methods. It is important to note that the wet-up of conductimetric sensors as described herein is extremely fast (on the order of milliseconds) because the sensor is comprised simply of two metal electrodes directly in contact with the fluid. Hence, no extended wet-up of intervening membranes is observed.

Additional aspects of the data acquisition, manipulation and analysis are discussed in further detail in a later section, below.

5.2.1. SIGNATURE ANALYSIS

Figure 7:
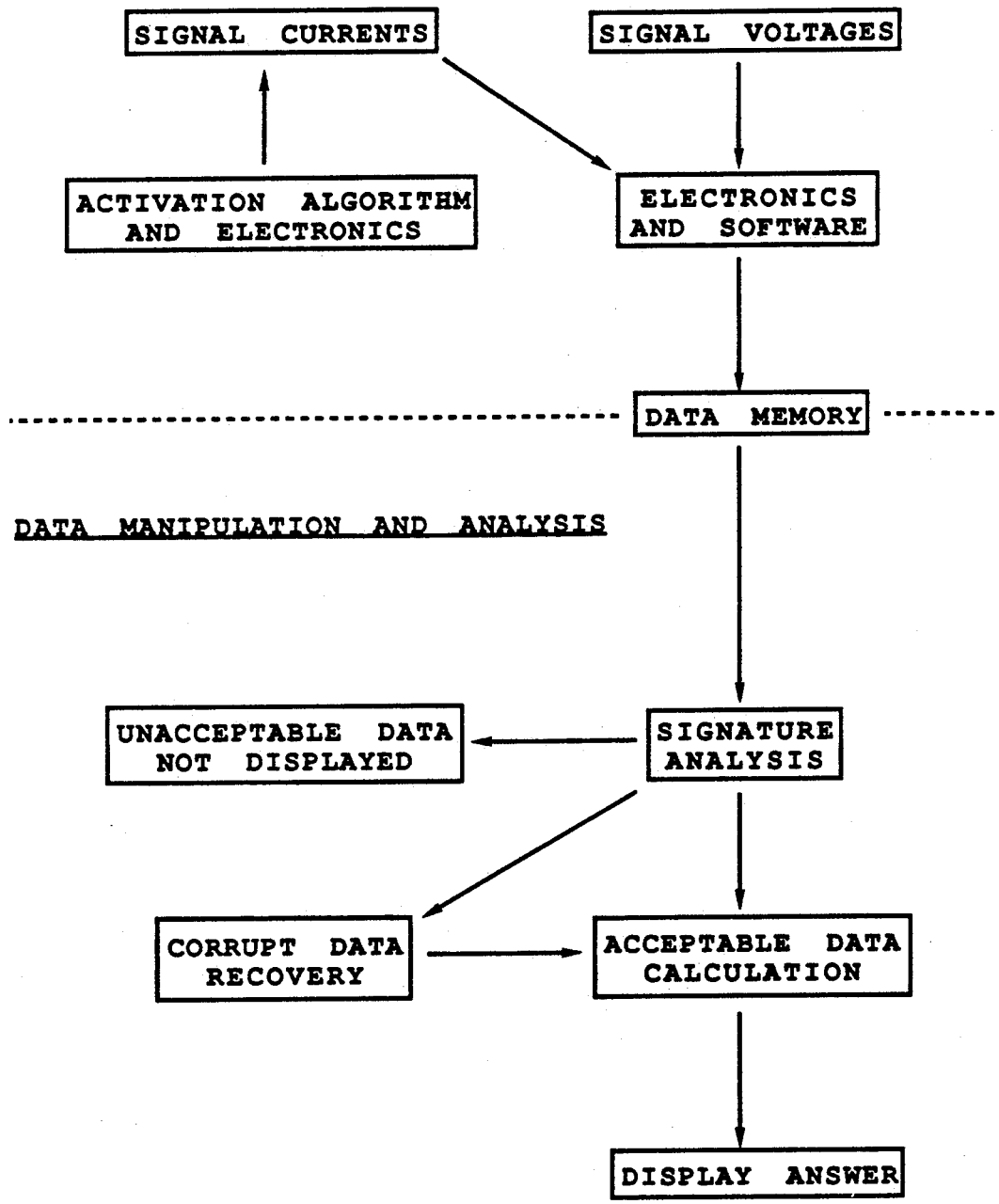
FIG. 7 illustrates a data handling method comprising a data acquisition portion and a data manipulation and analysis.

The signature analysis section of FIG. 7 is the step in which the integrity of the signal measurements, performed in the first and second data time windows, is analyzed. The computational methods used in this section detect the presence of excessive wet-up RC time constants, spikes, glitches and noise and compare the values observed within the time windows with preferred values held in memory.

In a specific embodiment of the present method, the first part of the signature analysis is run in real time (i.e., during data collection) in which a seven point sliding window slope analysis is implemented, beginning with the first seven points of the time window. A total of twenty-five data points (1-25) are actually collected in each time window, whether the measurements are taken in the presence of the first or second fluids. Although any size can be chosen for the sliding windows, the seven point sliding window provides an acceptable level of resolution.

The computational method is applied to each sensor during data collection at each time window. In an embodiment which utilizes an array of sensors, the computational method keeps track of which sensor is active and whether or not the time window has begun. The slope of each seven point window is computed, based on a recursive form of a linear regression. As each new point is collected, causing the seven point window to slide, the slope of the new seven point window (points 2-8) is compared with the first seven point window (points 1-7). A range of acceptable values for the new slope based on the value of the first slope (the basis slope) can be set, and if any window is found to fall outside that range, a bit is set for that sensor as a flag for later use.

The present sliding window slope analysis detects spikes and glitches in the time windows by looking at first derivative changes. It should be apparent that the slope of each new window can be compared with the slope of the window which immediately preceded it instead of comparing the new slope with that of the first seven point window. The latter option saves time, however, by avoiding the need to save in memory a new value for the basis slope with each pass through the computational method. Also, the present technique is more sensitive to low frequency glitches than the alternate approach which involves a trade-off in determining signal integrity. Yet another alternative method could compare the slope of both nearest neighbors rather than just the preceding point. Other methods should be apparent to those skilled in the art.

The second part of the signature analysis section involves a post-data collection processing computational method that checks for limits on the observed values. These computational methods may include the calculation of first derivatives, error or estimates of linear fit, delta drift rates, mean drift rates, second derivatives, degree of curvature and the like. That is, the computational method compares the observed data with the expected range of values held in memory. In a specific embodiment of the present method, limits are placed on the drift rate (the slope) of each time window, the difference between each time window's drift rate (i.e., the delta drift rate between the first fluid time window and the second fluid time window) and the mean or average value of the response obtained in each time window. The drift rate and mean values are obtained from a linear regression analysis. Maximum and minimum set values for each parameter may be different for each sensor. Moreover, an additional section of the post-data collection signature analysis computational method computes the error associated with the least squares fit and compares the value of this error with the limit placed for each sensor in the array. It is the selection of an optional combination of limits that determines the accuracy and precision that is attainable. For example tightening the noise limits but relaxing the wet-up RC time constant may be preferable over the reverse procedure.

Subsequent sections of the data manipulation and analysis portion of the data handling package dictates further actions if a particular sensors time window(s) contains spikes, glitches, noise or observed values (e.g., drift rates, delta drift rates, mean values or error of estimates) falling outside an expected range. The results of the affected sensors are not displayed and appropriate advisories are then displayed over the instrument monitor.

However, if the data contain manageable aberrations, a corrupt data recovery computational method is then employed to derive sufficient information to deliver a useful result. The corrupt data recovery computational method includes a determination of whether the detected glitch and/or spike is sufficiently large to affect deleteriously the propriety of the linear fit applied to the entire time window. This analysis is accomplished by comparing the linear fit applied to the entire time window to the basis slope obtained from the first sliding seven point window. Alternatively, the linear fits, with and without the offending glitch removed, may be compared and a decision made regarding its overall integrity. Still another recovery computational method implements a type of median filter to smooth detected glitches. Again, other recovery methods may be contemplated.

It may be useful, at this stage in the discussion, to describe briefly the behavior of a representative microfabricated sensor in the course of a typical fluid analysis cycle. FIG. 1 illustrates the potential response, as a function of time, of a potentiometric potassium ion sensor utilized in the present invention. During the first several seconds, the measurement cycle is initiated electronically, contact being made between the array of sensors, which are mounted preferably on a disposable assembly (See, for example, prior co-pending U.S. application Ser. No. 07/245,102, the complete disclosure of which is incorporated herein by reference), and the external computational means. During this initial period, all the sensors are grounded. Within a few seconds after the initial electrical contact is established, the first fluid is caused to flow over and make contact with the sensor array. As wet-up ensues the potential of the potentiometric sensor drifts monotonically, essentially in an exponential manner.

In the particular sequence illustrated in FIG. 1, the fluid change is made after about 72 seconds, though clearly, the introduction of the second fluid can be made much sooner if obtaining this potassium ion concentration is the only objective of the analytical cycle. In the present illustration, the first time window can be selected to fall at any suitable time after the first fluid is in place over the sensors and prior to the introduction of the second fluid. The second time window, in which the second set of signal measurements is performed, is begun preferably soon after the fluid change is made.

5.2.2. CALCULATION OF THE SENSOR RESPONSE

Calculation of the sensor response, that is, the change in potential reading between the first and second fluid (the delta voltage), is performed once an adequate data set has been obtained. The present algorithm used to calculate the sensor's response performs two linear least-squares fits. One least-squares fit is performed in the first fluid time window; the other is done in the second fluid time window.

There exists many different ways to extract the sensor response from a raw waveform such as that shown in FIG. 1. Some examples for deriving the delta response value include, but are not limited to, a linear/linear extrapolation, a linear/mean calculation, a mean/mean approach or a mean/linear method, to name a few. In the linear/linear case, the fit to the first time window is extrapolated forward to an estimated fluid transition point, the middle of the transition period. The fit to the second time window is extrapolated backward to the same estimated transition point, although clearly, it is not necessary to specifically select the fluid transition point at the midpoint as some other suitable point may also be selected. The arithmetic difference between these extrapolated voltages is the sensor's delta response. Alternatively, the ratio between the extrapolated values is calculated if currents derived from an amperometric sensor are being measured. The concentration in the sample fluid of the analyte species of interest can then be determined based on the known chemical activity (concentration) of the analyte in the calibrant fluid. The Nicolsky extension (1) of the Nernst equation, which also takes into account the effect on the sensor response of interfering ions present in the fluids, is used for this determination, in the case of potentiometric sensors:

$$E = E_o + RT/nF \log [A + \Sigma_{a,b} k_{a,b} B] \qquad (1)$$

where E is the measured electromotive force (signal), R is the gas law constant, T is the absolute temperature, n is the absolute value of the charge on analyte species a (e.g., n=1 for the ammonium ion). F is the Faraday constant, A is the activity of the analyte species a, B is the activity of an interfering chemical species b, $k_{a,b}$ is the interference coefficient associated with the effect of the presence of chemical species b on the electrochemical potentiometric determination of the activity of the analyte species a, and $E_o$ is a constant independent of T, A or B. For additional discussion of the Nicolsky equation, please refer to Amman, D. *Ion-Selective Microelectrodes*, Springer, Berlin (1986) p. 68 and references cited therein, the complete disclosures of which are incorporated herein by reference.

A correction of the calculated chemical activity of the analyte in the unknown or sample fluid can be obtained by applying the Henderson equation (2) where the term Ej is included in equation (1) and taking into consideration differences in ionic strength and matrix effects between the calibrant and sample fluids, which differences are usually manifested as a slight response of the reference electrode:

$$E_j = \frac{\Sigma_i [|z_i| \mu_i / z_i][c_i(\beta) - c_i(\alpha)]}{\Sigma_i [|z_i| \mu_i][c_i(\beta) - c_i(\alpha)]} \frac{RT}{F} \ln \frac{\Sigma_i |z_i| \mu_i c_i(\alpha)}{\Sigma_i |z_i| \mu_i c_i(\beta)} \qquad (2)$$

where $z_i$ is the charge, $\mu_i$ is the mobility, $c_i$ is the molar concentration of species i and $\alpha$ and $\beta$ are transfer coefficients.

For amperometric sensors, the concentration of the analyte in the sample fluid is derived from the measured current ratio, the known concentration of the preselected analyte in the calibrant fluid and a system constant. Equation 3 may thus be used:

$$[(i_1/i_2)c_1\gamma] + \delta = c_2 \qquad (3)$$

where $i_1$ and $i_2$ are the measured currents of the first and second fluids and $c_1$ and $c_2$ are molar concentrations of a preselected analyte. If the first fluid is calibrant, then $c_1$ is known and the value of $c_2$ in the sample can be readily obtained. The correction factors $\gamma$ and $\delta$ are derived experimentally and take into account differences in the physicochemical properties of the calibrant and sample fluids.

In the linear/mean approach, the linear fit to the calibrant time window is extrapolated forward, as before, but to the midpoint of the sample time window.

The difference between the extrapolated value from the calibrant fit and the mean sample value is the delta response. Again, the ratio of the extrapolated value of one time window to the midpoint value of the second time window can be calculated also, if desired. The mean/linear case reverses the direction of the extrapolation used in the preceding approach, and the execution of the mean/mean method of calculation should be fairly evident.

Ultimately, the method of choice for calculating the sensor response depends on the characteristics of that sensor and may be best determined through routine experimentation. However, the quality of the sensor response measurements will certainly have an impact on which method is most appropriate. For instance, a fairly large difference between the slopes of the data points in the first and second time windows may indicate that a linear method may lead to a skewed result and that a mean value of the particular time window may be more appropriate. As already discussed, above, the computational methods utilized during data collection, manipulation and analysis may be enhanced to look at drift rates (slopes) as data points are collected in each time window to determine the "smoothness" of the window. Likewise, first and second derivatives of fully sampled time windows can be compared using "enhanced" computational methods.

5.3. CALIBRANT FLUID

The calibrant fluid should contain a known concentration of the preselected analyte. The calibrant fluid may comprise a wet gas but is preferably comprised of an aqueous liquid. The chosen concentration of the preselected analyte in the calibrant is preferably similar to that expected to be encountered in the unknown sample. When necessary, preservatives (e.g., p-hydroxybenzoate, phenylmercuricacetate, p-aminobenzaldehyde and the like) may also be included to prevent microbial contamination. In the preferred method of the present invention, the calibrant fluid is an aqueous solution of several analytes whose concentrations are similar to those expected to be determined in an unknown sample, usually whole blood. It has been the experience of the inventors that, due to differences in the properties (e.g., viscosity) of the two fluids, the practice of the present method is simplified if a small volume of blood is used to displace a small volume of calibrant fluid. That is, the first fluid is preferably the calibrant, and the second fluid is preferably the blood sample. It should be evident, however, that the present method is not so limited, and the sequence and nature of the fluids introduced to the sensors is a matter of choice.

5.4. POTENTIOMETRIC SIGNAL RESPONSE

Although the signal response phenomena of an ion-selective electrode (ISE) upon change of the chemical composition of the fluid with which the electrode makes contact have been the object of much investigation in the chemical literature, the time-dependent signal of a dry-stored ISE upon first contact (wet-up) with an aqueous medium has received relatively little attention. As stated previously, this neglect results from the generally accepted view in the art that prior to attaining a complete equilibrated wet-up, the ISE can be of no analytical value. However, while this premise may hold true for conventionally fabricated macroelectrodes, it is not necessarily true for microfabricated devices.

Clearly, to obtain useful measurements as close to "real time" as possible, it would be very desirable to record analytical readings from dry-stored ISEs before the equilibrated wet-up process is complete. One means for obtaining this measurement involves the previously described prior art differential method in which a pair of electrodes with the same structure is used for each analyte species and corresponding calibrant solution. In such a configuration, there is no conventional reference electrode. The differential reading yields the ratio of unknown-to-known concentrations with regard to that particular chemical species to which that ISE is primarily responsive. Based on the assumption that each of the pair of ISEs is identical in the characteristics that give rise to the wet-up RC time-constant, e.g., physical dimension and material composition, the expectation that the monotonic wet-up signal will be canceled out of a differential measurement appears to be reasonable. Although an approach of some utility, it has certain inherent limitations with regard to rapid, multi-species electrochemical assays in parallel because it requires strictly simultaneous contact between each ISE of each matched pair and the calibrant and sample fluids, respectively. The problems associated with conducting and using an array of these matched pairs of ISEs for the analysis of multiple species would appear prohibitive as these pairs have been used only for single analyte determinations.

By the present method, such limitations are eliminated. The wet-up phenomena can be controlled to a high degree of confidence, along with the physical dimensions and material properties of the sensors and reference electrode. In the present invention the output shows that the wet-up has proceeded to a level where $\tau < t < 3\tau$ the slow rate of change can be treated as a linear drift and this linear relationship can reliably project the sensor's output forward in the time domain for some brief period, e.g., 30 seconds. This capability becomes crucial when one changes the solution in contact with the sensor and reference electrode, e.g., (unknown) sample (known) calibrant and compare the readings between the two fluids. In this manner the need for strictly simultaneous introduction of calibrant to the "reference" electrode and the unknown sample to the "working" electrode is circumvented.

It should be pointed out that even though a microfabricated reference electrode is likely to have its reference quality compromised by the eventual inward or outward diffusion of ionic species from the aqueous medium, this process is typically monotonic in the longer time domain. As a consequence, output of a sensor measured against such a reference electrode will be modeled reliably by a linear relationship. Linear relationships are generally preferred over higher order polynomials because of the basic simplicity, less vulnerability of the signal to interruptions, and greater confidence in obtaining a meaningful extrapolation involved with the former. Furthermore, it should be noted that the general exponential time dependence of such relaxation phenomena can be shown mathematically to be well approximated by a linear function at sufficiently large values of time. The propriety of this approximation becomes apparent if one notes that the Taylor series expansion of the experimental function is dominated by the linear terms as the argument $(-t/\tau)$ approaches $(-\alpha)$.

A series of FIGS. (1-3) follows to illustrate the wet-up dynamics of several different wholly microfabricated sensors with respect to a fully wet-up conventional flow through silver-silver chloride reference electrode, as well as the performance of such sensors versus a microfabricated reference electrode that undergoes similar wet-up effects. It can be seen that a linear fit of the reading in one fluid enables one to predict accurately what the value of the reading should be at later times for comparison with a subsequent reading in a second fluid.

It is important to characterize the wet-up behavior of a dry-stored, thin-film ion selective electrode upon exposure to a calibrant fluid. As illustrated in FIG. 1, after the grounding path is eliminated and a fluid path is established between the potassium sensor and the reference electrode (at about 9 seconds interval), the raw waveform becomes more manageable. The exponential decay of the potential output toward a steady-state value is a function of the wet-up of the potassium sensor and its inherent RC time constant.

FIGS. 2a to 2e show the response characteristics for a potassium, sodium, chloride, urea and on-board microfabricated reference electrode, respectively, versus a standard Corning reference electrode, with the change from calibrant to the unknown (sample) fluid occurring after about 50 seconds. (In these and subsequent Figures the response of the sensor prior to introduction of the calibrant fluid is not shown.) The wet-up response for all of these ISEs is similar, showing a roughly linear drift rate after about 40 seconds. It is particularly important to note that the on-board microfabricated reference electrode (FIG. 2e) does not respond to the fluid change, beyond minor correctable ionic strength and matrix effects. Hence it may be used advantageously as the actual reference electrode for the potassium, sodium, chloride, and urea sensors. In FIGS. 3a-3d, the data corresponding to these respective sensors in which the microfabricated reference electrode is used as the on-board reference demonstrates that, indeed, the on-board reference electrode operates perfunctorily and that the glitches associated with fluid change in FIGS. 2a-2d are even eliminated. This result is observed due, presumably, to closer proximity of the on-board reference electrodes to the sensors.

In terms of the selection criteria for the type of computational method for data manipulation and analysis, an empirical approach can be employed which involves determining the accuracy and precision for each of the first order relationships. A Linear/Linear method is found to be superior for the potassium, sodium and chloride sensors. The urea sensor, which has a slower response-time, provides best results when a Linear/Mean fit is used. The exact location and duration of the data acquisition windows can also be determined in this fashion.

5.5. AMPEROMETRIC SIGNAL RESPONSE

Unlike potentiometric measurements where the ideal sensitivity of the response of a sensor is determined by fundamental constants and intensive thermodynamic quantities via the Nernst equation, the current output in amperometric measurements is system dependent. That is, the result is dependent upon the geometry and transport properties of the overlaid structures, as well as the surface properties of the electrode. However, over some specific concentration range the current response will be directly proportional to the bulk concentration of the analyte. However the absolute current at any given bulk concentration usually increases over the time domain, as the dry-stored overlaid structures hydrate; that is, the transport rate across the membranes increases. This process can compromise the analytical value of the sensor, limiting its achievable accuracy and precision, unless the calibration process and subsequent measurement in a sample (unknown) fluid are performed close together over the time domain. Clearly, the operation of dry-stored, single-use amperometric sensors require that the sequence of steps performed over the course of the measurement be controlled in a careful fashion.

In a preferred embodiment of the present invention, at least two amperometric sensor signals (e.g., current output) are determined in each data aquisition time window (again, there should be at least two time windows, one for each fluid). Most preferably, one of the sensor signals determined in each time window (e.g., the calibrant fluid time window) is measured at a first applied potential and the other of the sensor signals, still in the same time window, is measured at a second applied potential. A fluid change is then made, and the above signal measuring process is repeated. If, for instance, the applied potential is stepped up from one value to a higher applied potential in the first time window, then in the second time window, it may be convenient to step down from that higher value to a lower applied potential.

The range of applied potentials at which the individual signal measurements may be varied according to the needs of the particular application. In the case of a glucose sensor, such applied potentials may be chosen to lie in the range of about 100 to about 300 mV. Most preferably, the one of at least two signal measurements in a given time window is carried out at an applied potential of about 125 mV and the other measurement at about 225 mV. The signal values obtained at each applied potential is then plotted on a signal (e.g., current) versus applied potential curve and the slope of the line defined by such values calculated and compared for each time window. In this manner, the slope of the line obtained for a calibrant fluid having a known concentration of a preselected species may then be compared with that recorded for a line derived from a sample fluid.

Figure 4:
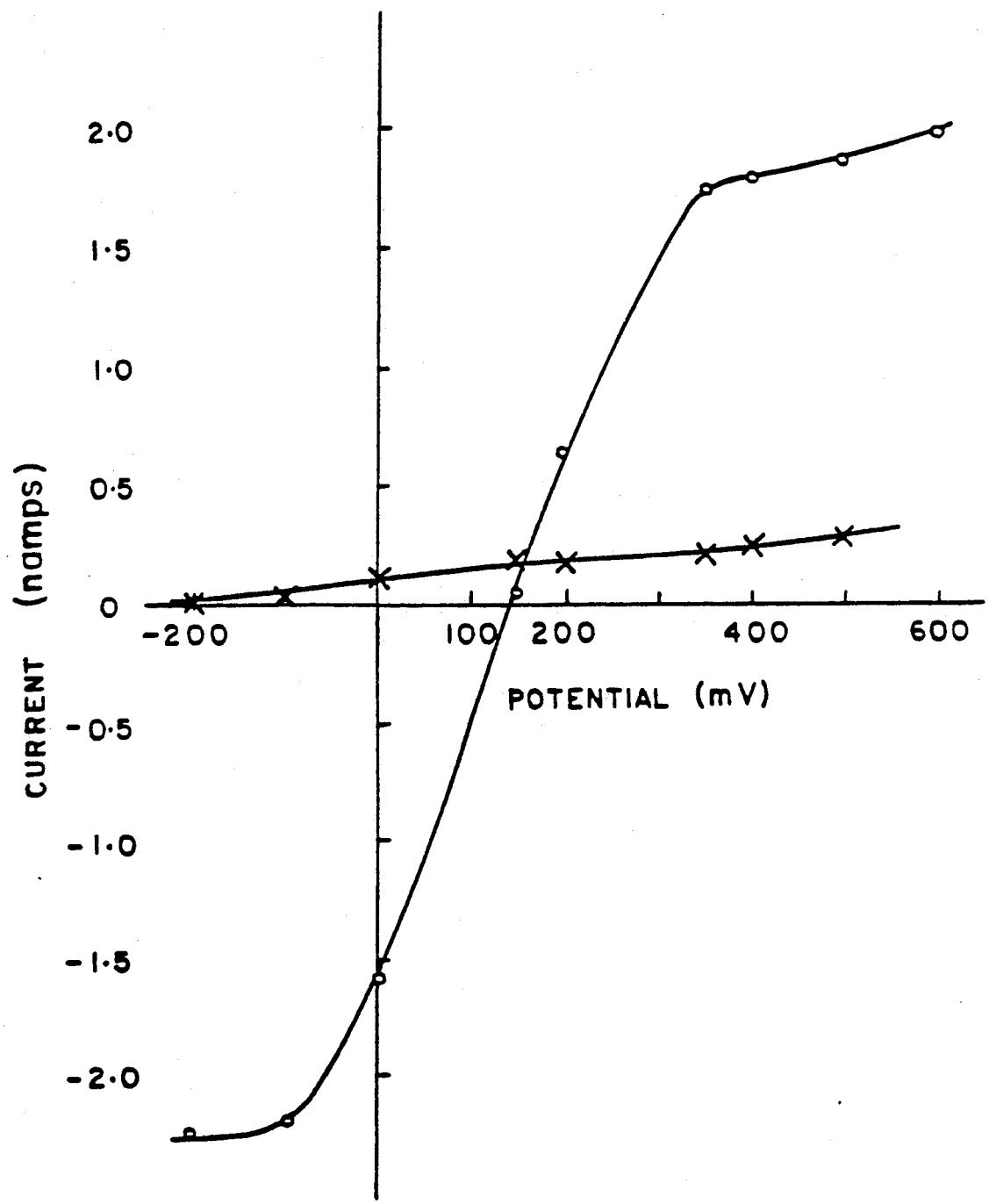
FIG. 4 shows the signal output (current in namps) of an amperometric glucose sensor, suitable for use in the present method, in response to the applied electrode potential (mV) using a 20 mM glucose in HEPES buffer sample (O) or a HEPES buffer only (X).

As a further illustration of the present embodiment, the attention of the reader is directed to FIG. 4 in which is shown an example of just such a signal versus applied potential curve described immediately above. On examination of the region of the curve lying between about +100 to about +200 mV, one notes that a small net positive current can be measured as the electrocatalytic oxidation of hydrogen peroxide is not quite counterbalanced by the corresponding reduction process. It is clear, however, that in this region, or any given region between about −100 to about +350 mV, the slope of the curve due to plain HEPES buffer (X) is significantly different from that of the curve due to a solution of 20 mM glucose in HEPES buffer (O). In fact, the slope of each curve is directly related to the concentration of glucose in each of the different fluids.

Preferably, the applied voltages are centered about the region in which the net current is or close to zero. In this way, the contribution of interfering redox processes to the total current or the effect of any bias current associated with measuring electronics is minimized, and the best estimate for the maximum slope is obtained.

5.6. SENSOR ACTIVATION

The mode of operation can be especially complex for amperometric sensors which are active devices, unlike potentiometric sensors which are electrically passive. An amperometric sensor measures the rate of electron transfer across the electrode-solution interface. Usually the electrode surface plays a catalytic role in such electron transfer (redox) reactions; therefore, the current is not only dependent upon the surface area of the sensor but also upon the catalytic activity of the surface.

It is not uncommon for electrode surfaces to be contaminated or deactivated. While a catalytic iridium surface, acting as the base sensor for a glucose electrode (See, for example, prior U.S. application Ser. No. 07/432,714), is highly active towards hydrogen peroxide oxidation prior to the deposition of overlaid structures, its catalytic activity is much reduced after such processing. The following procedure is designed to recover most of the sensitivity of the deactivated metal surface without damaging the established overlaid architecture.

5.6.1 METHODS FOR GLUCOSE ACTIVATION

The present novel operational method is useful for rapidly activating the electrode surface of a dry-stored amperometric glucose sensor without deleteriously affecting the overlaid structures. This activation makes an important contribution to reducing the overall apparent wet-up RC time-constant for the sensors. Unlike the prior art pulsing methods, which are always carried out during the analytical segment of the measurement (i.e., while the devices are fully wet-up and the pulses are related to data acquisition), the present activation is carried out in the presence of a non-corrosive fluid but prior to data acquisition and before the sensor has attained a fully wet-up state.

To activate the structure, a set of pulse groups is applied to the glucose sensor in the presence of the calibrant or sample fluids. This process comprises changing (cycling) the applied potential between values of opposite sign (e.g., $+1$ V to $-1$ V). The pulses are applied conveniently at full increment steps (i.e., at full $\pm 1$ V steps). However, it should be apparent to those of ordinary skill that such cycling may also be accomplished in a variety of other ways including, but not limited to, (i) pulsing; (ii) intermediate incremental steps to the desired positive potential, followed by intermediate incremental steps to the desired negative potential; (iii) linear potential sweeps to the respective desired potentials; and (iv) non-linear potential sweeps or such sweeps which resemble smooth sinusoidal waves.

Figure 5A:
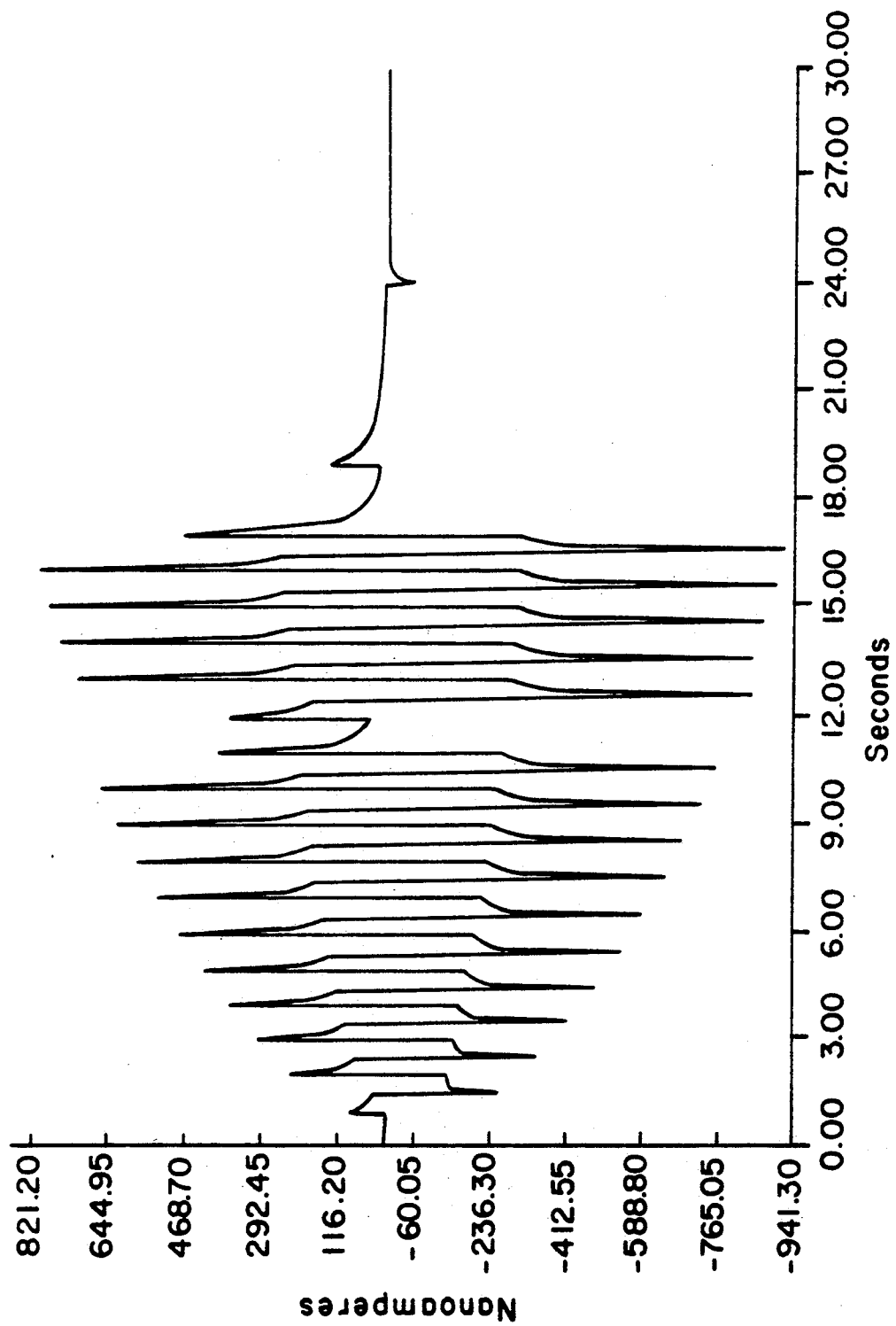
FIG. 5a shows the increasing current output of a microfabricated glucose sensor as a series of activating pulse groups or potential changes are applied.
Figure 5B:
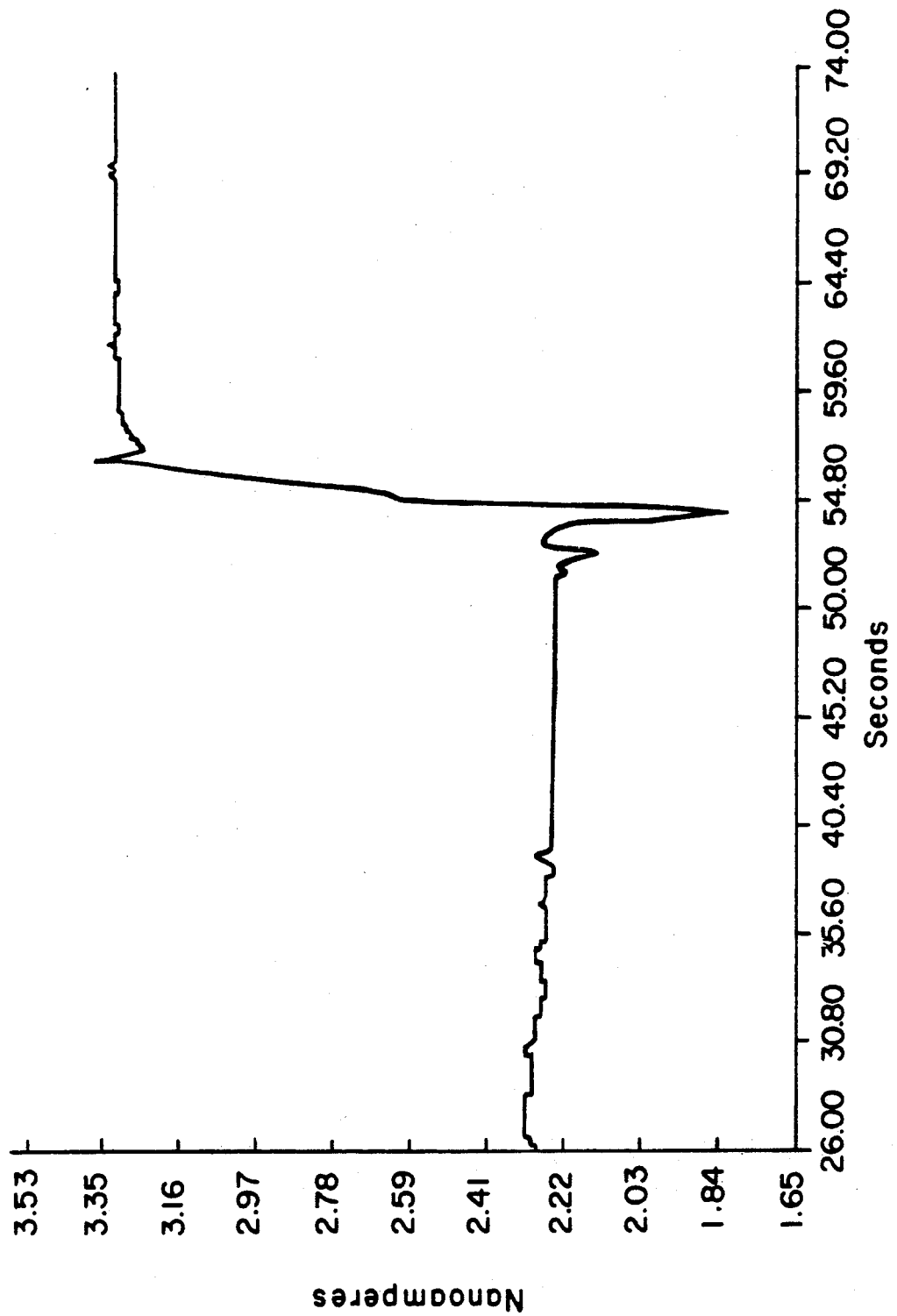
Figure 5C:
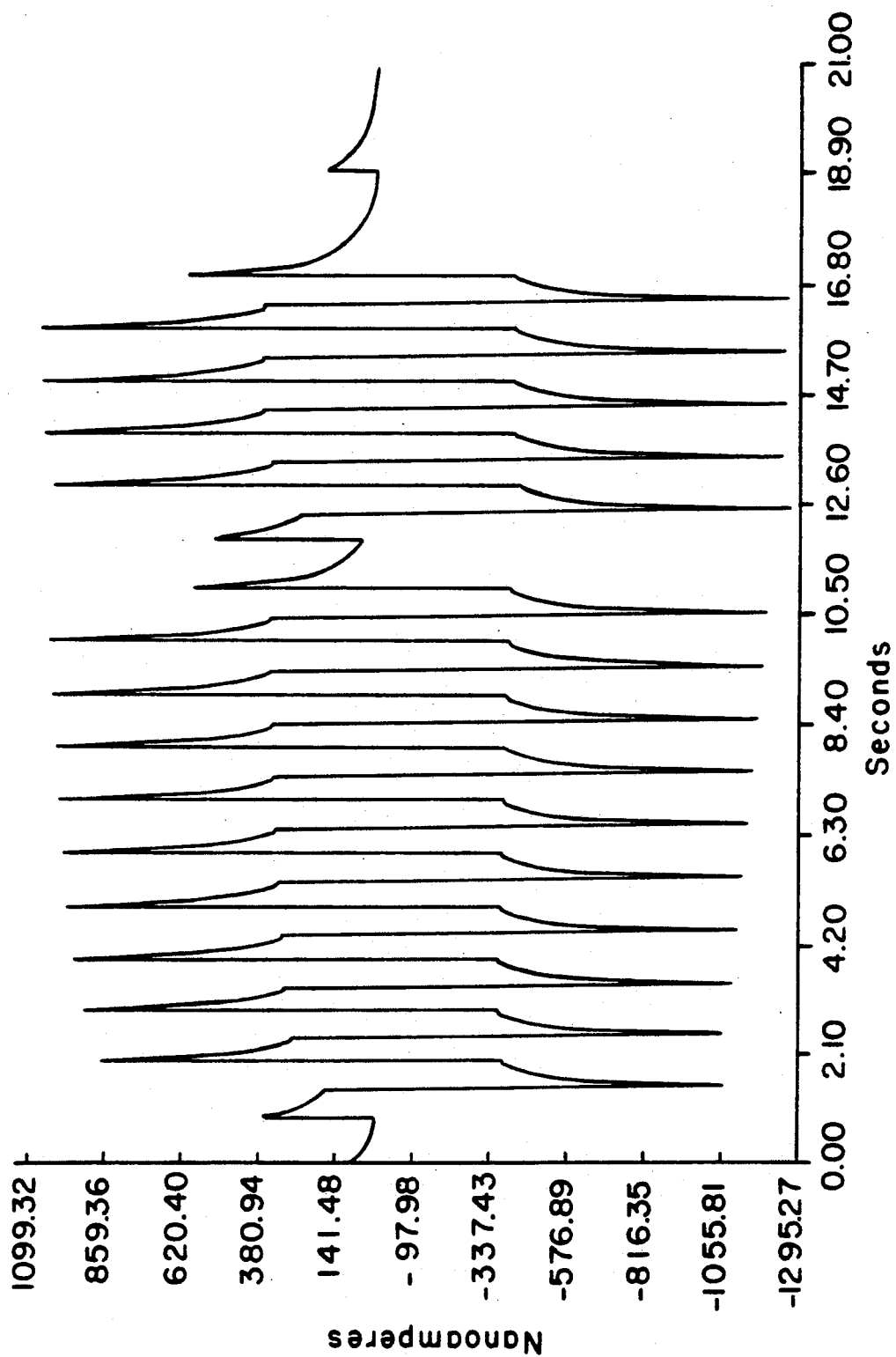
FIG. 5c shows the absence of any substantial change in the current output of the activated glucose sensor of FIG. 4a upon application of additional pulse groups.

Broadly, the first two pulse groups in the set have a magnitude and duration sufficient to activate the catalytic surface of the electrode. These pulse groups may also promote hydration of the overlaid structures. The third pulse group in the set serves to reduce the initial rate of change in current upon application of the actual operating potential. Referring now to FIG. 5a the time zero corresponds to the time at which the sensor comes into contact with the fluid, calibrant in the preferred instance), one observes that during the application of the first two pulse groups, the peak currents for hydrogen peroxide oxidation and reduction increase dramatically. FIG. 5b shows in more detail the response of the activated sensor, at the operating potential, to a 5 mM glucose calibrant solution (26-53 sec) followed by a 10 mM human serum (from about 54 sec). The analytical value of the glucose sensor is clearly apparent, with a significant current being observed for both fluids and in which the current shows an increase after the sensor is exposed to a biological fluid having a glucose concentration which is higher than the calibrant solution. At an operating potential of $+350$ mV, the sensor gives a linear current response at a range of 0.1-30 mM glucose. FIG. 5c, suggests that the sensor is almost fully activated because there is only a marginal increase in the maximum hydrogen peroxide oxidation and reduction currents when the entire pulsing sequence is repeated on the same sensor.

A viable alternative to cycling the applied potential, involves galvanostatic control over the sensor activation with a constant current source being applied to the sensor until the required potential attains some predetermined value or rate of change.

Another alternative for measuring the current output of the sensors, to determine its level of activation, involves making a conductivity measurement between two electrodes, one which is the sensor.

In one embodiment of the present method the pulsing sequence for hydrogen peroxide measuring sensors are as follows: pulse groups 1 and 2 should be of a duration of about 5 seconds with limits of $+0.7$ to $+1.2$ V at the oxidizing end and $-0.7$ to $-1.2$ V at the reducing end, which pulses may or may not be applied symmetrically. A single extended negative pulse followed by the standard sequence may also be applied advantageously. The inventors have observed that negative pulses are an important aspect of the activation process, and they speculate that the activation process is likely to be associated with the reduction of one or more types of functional groups of the iridium electrode. However, the inventors do not wish to be bound by the present speculation nor do they wish to limit the scope of the present invention by making specific interpretations of the surface activation process on a molecular level.

The third pulse group should be selected from groups in which the final potential step is in the range $+400$ mV to $+800$ mV. As can be seen from FIG. 5b the current recorded for the 5 mM glucose calibrant fluid shows that the sensor has attained a sufficient degree of wet-up and activation. During the period from 46 to 52 seconds, data is recorded in the first time window for later extrapolation. After 53 seconds the calibrant fluid is forced to waste and the biological fluid (sample) placed over the sensor. An advantage of thin-film microfabricated biolayers is that the response-time (i.e., the time it takes for the current to change to a value which is proportional to the bulk concentration of the analyte in the second fluid) is fast, usually less than 5 seconds. It is this additional property of the present microfabricated devices that contributes to the success of the present analytical methods. During the period from 61 to 66 seconds, the data is recorded in the second time window.

As with the potentiometric sensors, the selection of an appropriate location for the data acquisition window and the choice of the data fitting computational method are based on empirical calculations of the accuracy and precision attainable with each of the fits. As with the potentiometric urea sensor a Linear/Mean fit is preferred for the glucose sensor.

5.6.2. OPERATIONAL METHODS GENERALLY

The discussion above relates to a glucose sensor comprising an iridium electrocatalyst at which hydrogen peroxide produced by an enzymatic reaction is measured by means of electrochemical oxidation at an operating potential of +350 mV versus an on-board silver-silver chloride reference electrode. An alternative method for operating this sensor is based upon electrochemical reduction of hydrogen peroxide. This operation is achieved by applying an operating potential in the range of zero mV to −250 mV, preceded by pulse groups similar to 1 and 2 above, but with pulse group 3 having a final potential set in the range of −200 mV to −500 mV.

The operational methods described above can also be applied for activating sensors where platinum or another noble metal is used as the electrocatalyst in place of iridium; these surfaces also become deactivated during post-processing steps.

An oxygen sensor of the type disclosed in the U.S. application Ser. No. 07/432,714, with a gold electrocatalyst suitable for oxygen reduction, may also be operated with this type of activation method. However, it is sometimes desirable to modify the duration and magnitude of pulse groups 1 and 2 because different metal surfaces are deactivated to different extents during the deposition of overlaid structures and related processing steps. In addition, pulse group 3 is preferably chosen to fall in the range of −600 mV to −800 mV, where an operating potential in the range of −400 mV to −550 mV is contemplated for oxygen reduction at a gold electrode.

5.6.3. COMPUTATIONAL METHODS FOR ENZYME ASSAYS AND IMMUNOASSAYS

In a metabolite assay the object of the computational method is the determination of the bulk concentration of the metabolite. Clearly, the sensor should not perturb the bulk concentration of the metabolite if the measurement is to be of analytical value.

For an enzyme sensor or an enzyme-linked immunosensor-based assay, by contrast, the object of the sensor computational method is the determination of the rate of change in concentration of an electroactive species which is consumed or produced while the assay is in progress, which rate reflects the enzyme activity present in the system. Sensors appropriate for enzyme and enzyme-linked immunoassays are disclosed once again in U.S. application Ser. No. 07/432,714.

Figure 6:
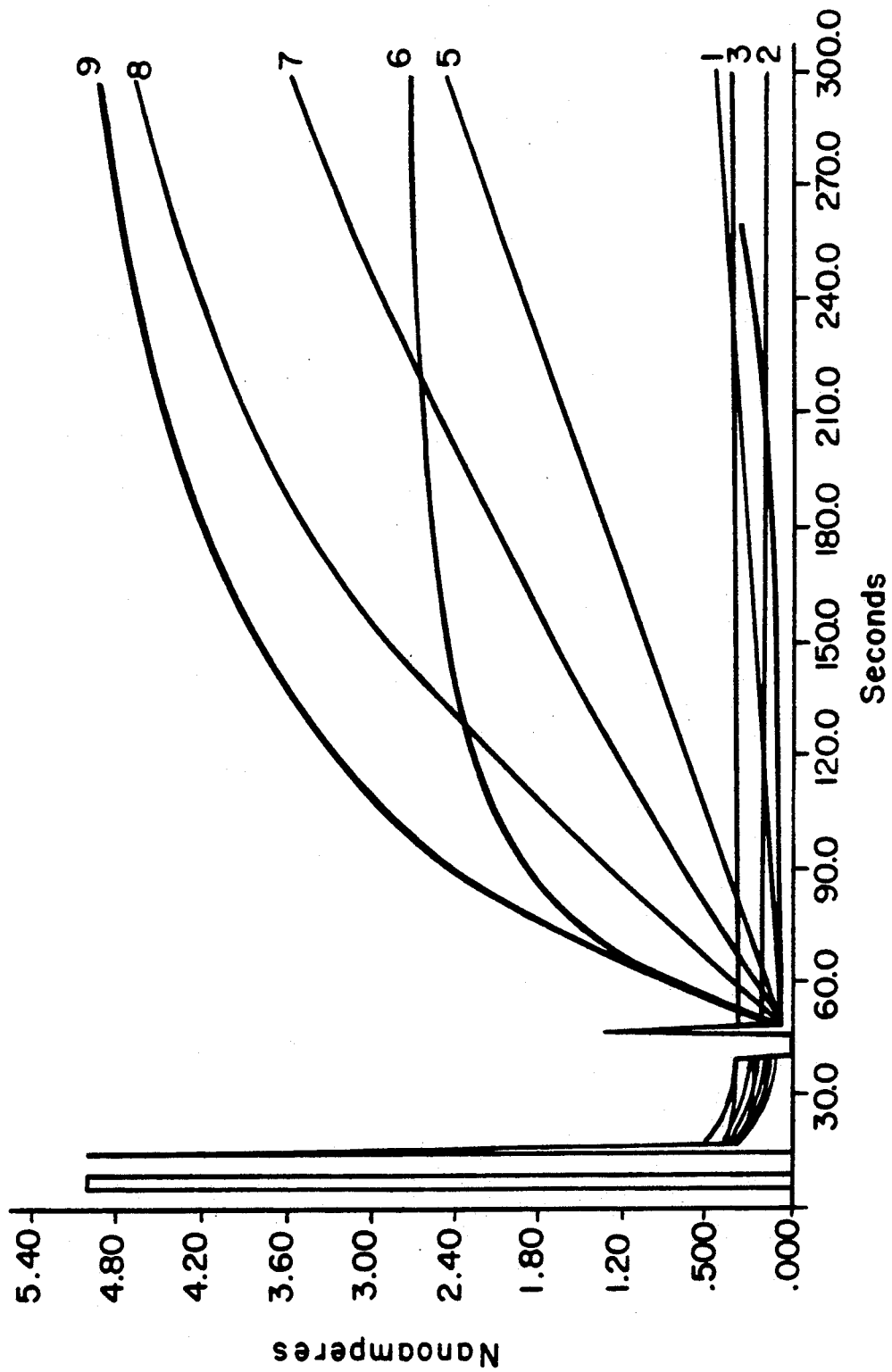
FIG. 6 illustrates an electrochemical creatine kinase enzyme assay based on initial rate measurements.

If the product of the assay is hydrogen peroxide (i.e., it is the electroactive species which is produced in the course of the assay), the computational method can be modified as follows: after a set of activation pulse groups is applied and measurement of a calibrant current is performed, as described above, substrates or reagents for the enzyme or enzyme-linked immunoassay are introduced to the sensor. After a brief induction or mixing period the current changes steadily, and the initial rate of change, di/dt, is then computed (See, FIG. 6). From the rate of change in the current and the known current electroactive species corresponding to a certain concentration in the calibrant, the rate of increase in its concentration can be estimated. This rate can be expressed as the enzyme activity, that is moles of substrate consumed per unit time at a certain temperature, pH etc. It is important to note that if the data collection period extends over several minutes, the above-mentioned pulse groups wet-up the sensor structure to a sufficient extent such that the calibrant signal can be readily extrapolated forward in the time domain. Otherwise the rate measurement, which is based on the initial sensor response in the presence of calibrant fluid (if calibrant is introduced prior to introducing the sample), may be severely compromised (Refer to earlier discussions related to the importance of making the calibrant and sample measurements close in time). The use of microfabricated immunosensors in this manner makes it possible to obtain rate measurements prior to the sensor attaining a fully wet-up state.

Another problem that is encountered when a sensor is operated over an extended period (2-3 minutes) is that product build-up or reaction depletion zones occur in the overlaid structures of the electrode with concomitant diffusion gradients extending out into the bulk solution. Such inhomogeneity close to the sensor can adversely affect its performance. For example, an excessive differential between the hydrogen ion concentration close to the electrode and hydrogen ion concentration in the bulk solution causes a shift in the activation energy for hydrogen peroxide oxidation. This shift may result in a non-linear current response. This problem may be circumvented by modifying the computational method to include additional sets of pulse groups at preselected time intervals. After applying the initial set of three pulse groups and the calibration has been performed, as described above, substrates or reagents for the assay are allowed to pass over the sensor. A measurement is then made in much the same way, as described above for glucose. However, after this measurement the pulsing sequence, or some modified portion thereof, is repeated and a second measurement is made. This sequence is repeated several times (usually five to ten) to yield a set of current measurements made at exact time intervals. The initial rate of change in the current may then be more accurately estimated from this set of current measurements because repeated pulsing has the effect of washing-out the electrode surface and overlaid structures and disordering the fluid layer and concentration gradients which lie close to the sensor. Again all of these processes are monitored on a sensor that is undergoing wet-up, i.e., $t \leq 3\tau$.

5.6.4. ADVANCED OPERATIONAL METHODS

Advanced operational methods can also be used to make the system "smart." Such methods can be applied during the real time operation of the sensors or during post data collection treatments. In particular, the flexible methods for governing the activation of amperometric sensors, assessing the propriety of a given set of data points or determining the best position for the data window may be incorporated, to name a few.

Thus, these methods may include alternatives to applying the identical pulse sequence to all amperometric sensors which may be present in the array. For example, the operational method can be modified such that pulse groups 1 and 2 are applied until the observed peak current associated with each potential pulse has reached a finite value, until the charge passed in each pulse has reached a finite value, until the charge passed for the entire pulse sequence has reached the finite value or until the RC time constant for the sensors after a given pulse is within some predetermined range of values. Moreover, pulse groups 1 and 2 may be applied until the rate of change between successive pulses, in terms of peak current, charge passed or RC time constant, is within some preselected range.

Advanced methods for error recovery can also be implemented. In particular, computational methods can be put in place for detecting the presence of glitches in the data set, whether such glitches are isolated or numerous, or whether they may be associated with common background noise. An advanced method for sensing integrity failures may suggest appropriate solutions, such as the application of median filters. Alternatively, another data set may be chosen which is derived from a separate data window stored in the system. For example, if the sample causes an abnormally slow response from the sensor, gives rise to non-ideal waveforms upon contact with the sensors or, generally, does not provide well-behaved waveforms, the first and second time windows may not be positioned in the best place initially. The presence of slight defects in the sensor may also give rise to less than desirable responses. In the case of a slow response, the maximum value for the sample or second fluid may not have yet been reached before a second signal measurement is performed (i.e., a second time window is selected for comparison with the first time window associated with the first or calibrant fluid). The signal associated with the sample may degrade rapidly soon after reaching the maximum value, thus providing a lower value than what should have been observed if the signal had not degraded.

In both cases discussed in the preceding paragraph, the computational method may search for the proper data collection window and locate the maximum value which provides a better estimate of the concentration of the preselected analyte species. Also, even if certain error limits are reached or exceeded, a reinspection of the value of the slope and the quality of the overall drift may prompt the instrument to accept the values obtained. In certain cases, the value of the delta drift can override a data window with an unusual number of glitches or a high level of noise. Of course, different methods for extrapolating the slopes and calculating the difference between the signal measurements may be selected. These non-ideal responses may be encountered more frequently with sensors of increased functional complexity.

As mentioned earlier, one may also conceive of flexible computational methods adapted to determining when and whether a sufficient number of data points has been collected. Such advanced methods may decrease the time necessary for carrying out the data collection and analysis.

5.7. CONDUCTIVITY MEASUREMENTS

For a colloidal suspension such as blood, the electrical conductance is a function of the nature of the particles, the medium and the fraction of the total volume occupied by the particles. At high particle concentrations, as in blood, it is also necessary to take into account the geometry and orientation of the particle.

The entire period of data acquisition in the calibrant and in the blood takes only about one second. During this period the a.c. conductivity is measured at a frequency which is selected to be sufficiently high to minimize the impedance at the sensor-fluid interface, and sufficiently low to minimize capacitive coupling across the erythrocyte cell membrane. A preferred frequency is about 50 KHz.

Once the calibration has been made, the calibrant fluid is then removed and blood introduced. The measurement cycle is then repeated with the actual measurement time being selected so that the blood is in a quiescent state, but before a significant degree of erythrocytes have settled.

The conductivity sensor comprises two noble metal electrodes microfabricated on a planar surface and designed with the appropriate geometry.

For conductivity measurements there is no need for a sophisticated computational method for performing a signature analysis. Calculation of the percent hematocrit in the blood is made either from an empirically determined calibration curve stored in the electronics or, more preferably by means of an equation developed by Velick and Gorin as described in *Journal of General Physiology* 1940, 23, 752-771.

Such conductivity measurement may also be utilized to determine the success or failure of the fluid change operation. That is, stored values of predicted fluid conductivities can be compared to the observed measurements to provide a quality assurance method for detecting the presence of an adequate intervening air segment between fluids, the failure of the calibrant fluid to move to waste, or other such system failures associated with the fluidics movements.

5.8. SYSTEM INTEGRATION

As alluded to elsewhere in this disclosure, a system most attractive in the clinical setting is not limited to discrete measurements of single analytes. Instead, an array of sensors, designed to make a multiplicity of discrete measurements of a range of different analytes in biological fluids is preferred. This array of sensors is preferably exposed to a single, common calibrant fluid which is removed after all of the sensors have been calibrated. Only then can the second (sample) fluid be introduced to the sensors. Such an integrated setting means that all of the sensors must be chemically and electrically compatible: that is, they must wet-up and respond at approximately the same rate without interfering with one another. Thus, sensor compatibility and system integration is enhanced if the pulsing sequence, used in amperometric measurements, is completed prior to performing potentiometric measurements because the high current flow in solution associated with pulsing can undermine the integrity of the potentiometric signal.

Also, when the conductivity sensor is activated, a current of ca. $10^{-3}$ A, flows in the solution between the pair of metal electrodes. While this current may seem small, it is about six orders of magnitude greater then measured in the amperometric based analyses. Again, during the period when the amperometric sensors are being pulsed, a maximum current of, ca. $10^{-6}$ A, also flows. To minimize interference during calibration between the conductimetric and amperometric sensors, it is preferable that the conductivity sensor be operated after activation of the amperometric sensors but before amperometric data are acquired. After the fluid change, the amperometric data acquisition is performed before the second conductivity measurement is made. A series resistor, ca. $10^5$ ohm, may also be used to protect amperometric sensors during the a.c. conductivity measurements.

As mentioned previously, the conductivity sensor may also be used to distinguish the general composition of a fluid, i.e., whether the sensor is in contact with calibrant fluid, serum or whole-blood, or for that matter no sample at all, i.e., air. Because many of the sensors display matrix effects, as discussed previously above, this measurement may be used to make the appropriate correction to the calculation of the concentration of the preselected analytes.

In terms of the integration of conductivity measurements with potentiometric measurements, there is no discernable interference. However, it is preferred that the conductivity measurement be avoided during data acquisition at the potentiometric sensors.

In addition, it is preferred that there exists a fluid grounding electrode in close proximity to the potentiometric sensors to absorb excess charge generated in the fluid when the conductivity sensor is activated. This excess charge may have the undesirable effect of polarizing the potentiometric membranes. Moreover, the membranes must be depolarized rapidly if they are to be of analytical value.

Finally, it may be desirable to place the conductivity measuring sensor on a separate chip from that of the potentiometric sensors. Commonly, these sensor structures are actually fabricated on a silicon wafer with an insulating layer, ca. $0.5 \cdot 10^{-6}$ m in thickness, of silicon dioxide. The underlying silicon is a semiconductor which means that capacitive coupling between sensors presents a possible signal interference. Separating the sensors on different chips obviates this potential problem.

6. EXAMPLES

Figure 8:
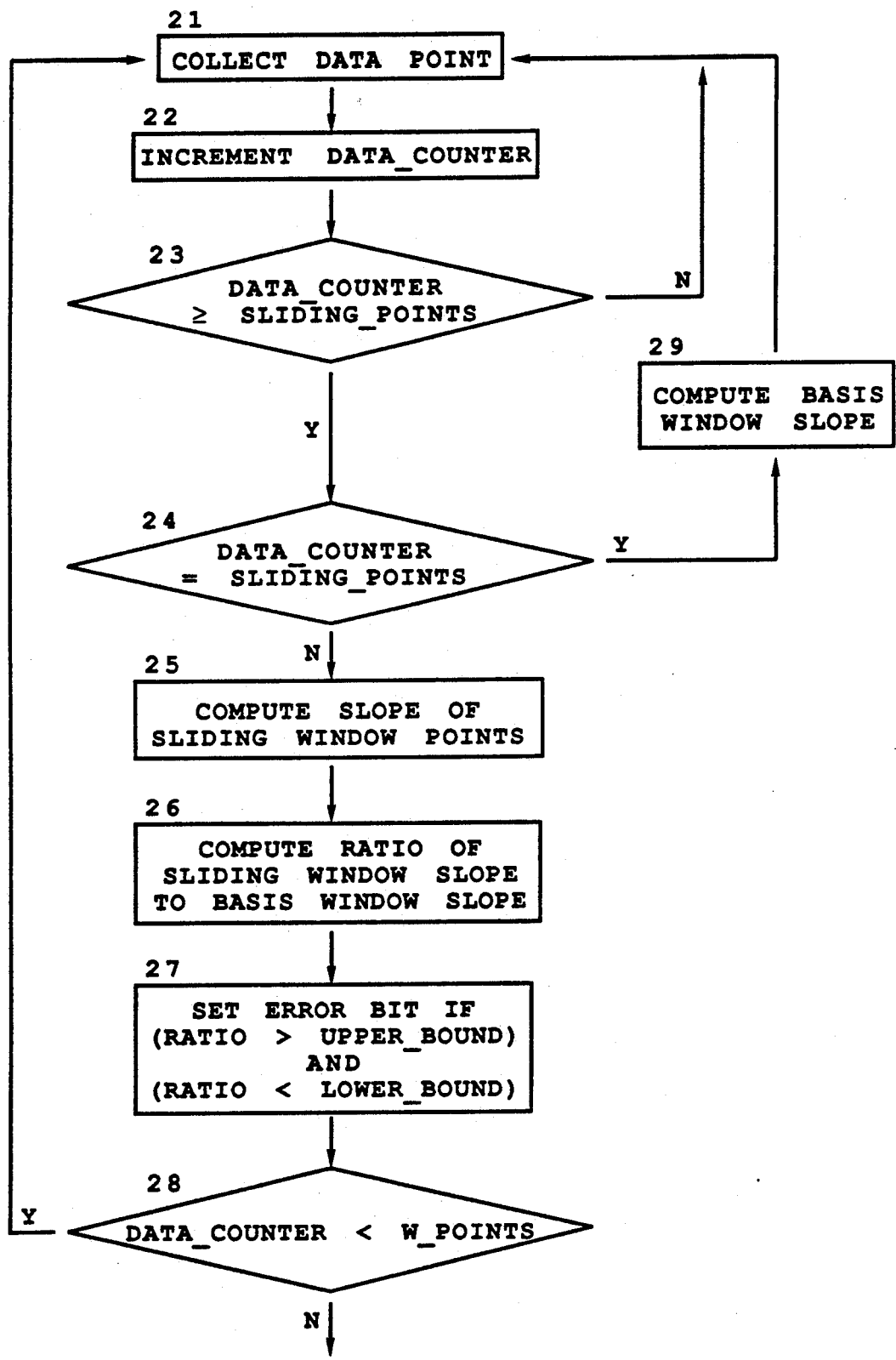
FIG. 8 illustrates a detailed flow chart of a data collection system.

As a further illustration of the present method, the following example is described. Referring now to FIG. 8, there is shown a more detailed flow chart of the Data Collection method. As mentioned previously, data collection may be accomplished in several different ways, including simply sequentially measuring and storing data. The method of the preferred embodiment permits verifying integrity of the measurements in real time, while collecting input data. Although a thorough data integrity analysis is provided at the Data Analysis stage, this on-line verification method permits early detection and, possibly, elimination of spikes, glitches, and other noise in the data. Alternatively, time windows can be determined intelligently at flexible intervals where the data points are not significantly affected by noise. Such smooth time windows can thus be located readily.

In the present example, the Data Collection process begins at block 21, where each data point is measured. Data acquisition involves taking an analog signal and recording it in digital format in the appropriate memory location. To ensure that the system is not susceptible to 60 cycle noise, a set of 80 data points every one-sixtieth of a second are preferably recorded. (Clearly in countries where 50 cycle noise is the norm the sampling rate is set at 80 data points every one-fiftieth of a second). The average value of this set is then calculated, and this value is taken as a "single" data point. These "single" data points are then used in further calculations.

As described above, the electronics are designed to be appropriate for high impedance potentiometric sensors with sufficient resolution over the expected range of measurements. The electronics for amperometric sensors includes current to voltage convertors designed to have sufficient resolution over the expected range of current measurements.

Next, the method flow passes to block 22, where a counter (DATA_COUNTER), which keeps track of the aggregate number of data points collected within a time window, is incremented by one. (The DATA_COUNTER is initialized to zero prior to acquisition of the first data point of a given time window.) The method flow then passes to test 23, where the total number of collected data points (DATA_COUNTER) is compared to the number of data points of a selected sliding window set (SLIDING_POINTS). The size of a sliding window is selected on the basis of a trade-off between the computational time and precision of error detection. In this instance, a seven point sliding window is selected from a twenty-five point time window. According to test 23, if the total number of acquired points is less than the size of one sliding window, the control returns to block 21, where another data point is acquired. Otherwise, control is transferred to test 24.

Test 24 is provided to locate the basis window. In this instance, the basis window is defined as the first sliding window, and remains the same throughout the data acquisition process for a given time window. It should be apparent to one of ordinary skill in the art that there are other methods of selecting a basis window. For example, a basis window can be defined as a sliding window which is "behind" the current sliding window by one or more points.

According to test 24, if an exact number of SLIDING_POINTS are collected, method flow is transferred to block 29; otherwise, the total number of collected points is greater than the size of one sliding window, and method flow passes to block 25. At block 29, the slope of the basis window is computed using a linear regression (i.e., by fitting points into a line defined by $y = ax + b$, wherein the slope is "a"). At block 25, a new sliding window set is formed and a recursive form of the linear regression method is used to compute the slope of a sliding window. In this instance, a new sliding window set is created whenever flow enters block 25. Therefore, a first sliding window consists of the following data points: {2, 3 . . . (SLIDING_POINTS+1)}, and each subsequent sliding window is formed by including a newly acquired data point and eliminating the first data point of the previous sliding window set.

Next, the method flow passes to block 26, where the slope of the basis window is compared to the slope of the current sliding window, and the ratio of the slopes is computed. Then at block 27, the integrity of a current sliding window data set is verified. If the ratio of the slopes is not within acceptable bounds, the output of such sensor is deemed to contain an error. One can set, for example, an upper bound of 2.5 for the ratio. If, however, the basis window has a value of zero, a difference instead of a ratio is used.

Hence, if the ratio or difference is out of bounds, a flag (ERROR) is set. In this instance, the ERROR flag is simply a bit. Alternatively, the ERROR flag value might contain a pointer to a specific data point that causes the ratio of the slopes to be out of bounds. Next, the method flow enters test 28, which checks whether additional data points should be measured for a given time window. If all the time window points (W_POINTS) have not been collected, the flow returns to block 41; otherwise, the control is transferred to a new process step which causes the displacement of the calibrant fluid by the sample fluid, with an air segment present between the fluids. When the last time window has been collected, the following data analysis stage is carried out. It should be apparent that W_POINTS are collected for each active sensor in the array. Thus, each process block of FIG. 8 is performed essentially in parallel for each active sensor.

Figure 9:
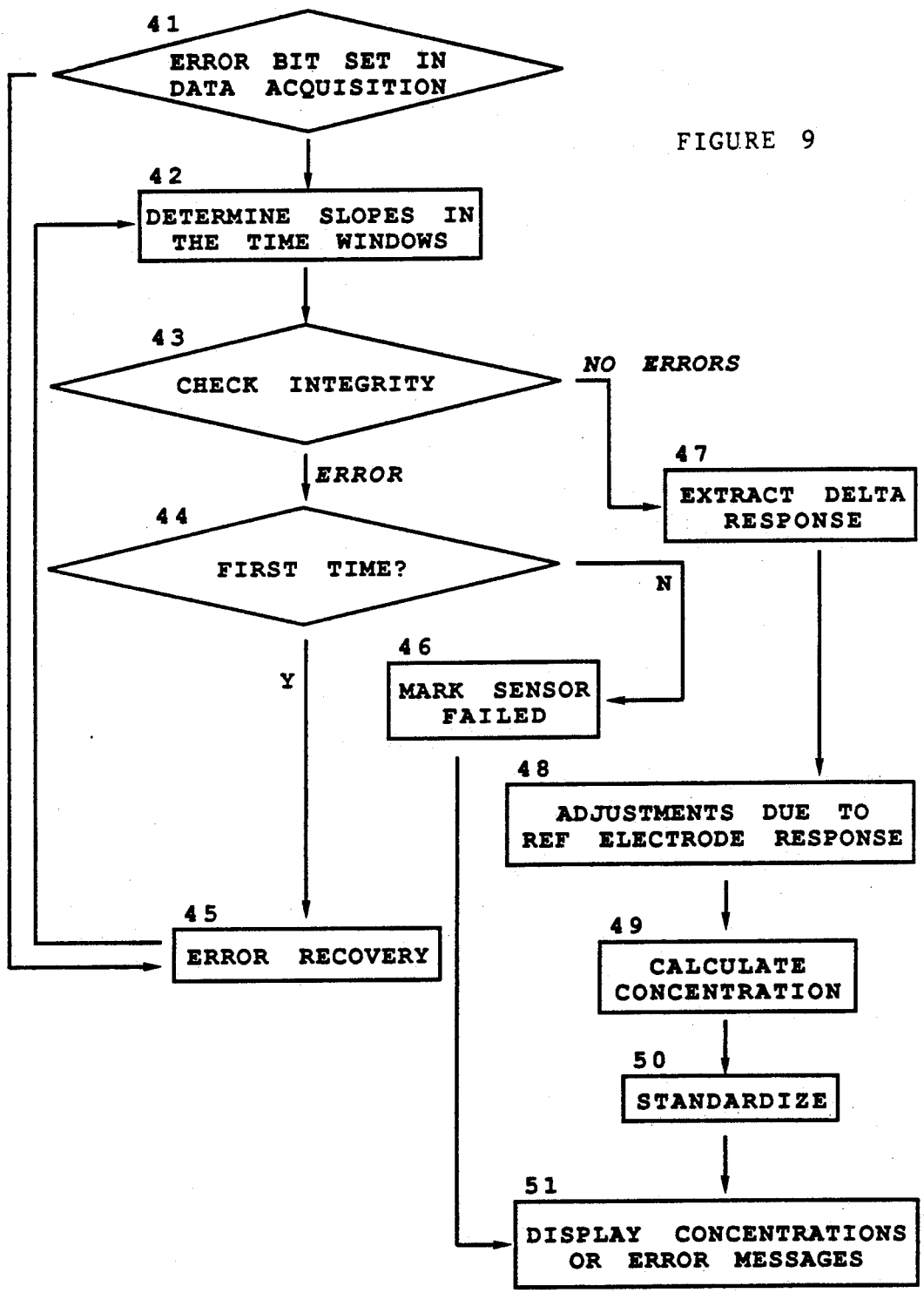
FIG. 9 illustrates schematically the steps of Data Analysis stage of the method in which analyte concentrations are determined for each sensor measurement. This figure also shows the sensor response to a fixed concentration of adenosine triphosphate (ATP), the product of the enzymatic process.

FIG. 9 shows schematically the steps of the Data Analysis stage of the method in which analyte concentrations are determined from each sensor measurement.

At this stage, data points for the first (e.g., calibrant) and second (e.g., sample) time windows have been collected and stored in appropriate memory locations. Test blocks 41-47 occur for each active sensor in the array, while test blocks 48-51 occur once for the entire array.

The process begins at test 41 which checks whether an error has been detected at the Data Acquisition stage by testing the status of the ERROR bit. If the ERROR bit is set, method flow passes directly to block 42, where error recovery is performed. Otherwise (i.e., no errors at Data Acquisition stage), flow passes to block 42.

At block 42, a linear regression is applied to the data points of each window to approximate the drift rates (slopes) of the data window. A linear least squares fit is a well known method of interpolation, in which data points are connected to approximate a line, "$y = ax + b$," where constants "a" and "b" are chosen such that the sum of squares of the deviation from the actual data points is minimized. Alternatively, higher order regressions, i.e., those that approximate 2nd, 3rd, . . . , nth order functions, can be implemented easily. Generally, the order of the applied regression should be determined according to the nature of the sensors' degree of wet-up and waveform in the selected time window intervals.

Next, the flow passes to test 43, where the data points of both windows are checked for unexpected values. The following data integrity verification is then performed:

MIN_SLOPE < first window slope < MAX_SLOPE MIN_SLOPE < second window slope < MAX_SLOPE (first window slope-second window slope) < MAX_DIFF MIN_MEAN < first window mean value < MAX_MEAN MIN_MEAN < second window mean value < MAX_MEAN_1 first window error of approximation < MAX_ERROR second window error of approximation < MAX_ERROR The values, MIN_SLOPE, MAX_SLOPE, MAX_DIFF, MIN_MEAN, MAX_MEAN_1 and MAX_ERROR are expected ranges of the above parameters. The specific values are determined experimentally, based on the predictable characteristics of the sensors' response curve. Table I lists some suggested values for the various data window parameters.

TABLE I

SUGGESTED LIMITS FOR VARIOUS DATA WINDOW PARAMETERS

| SENSOR | SLOPE (mV/s) min | SLOPE (mV/s) max | MEAN (mV) min | MEAN (mV) max | ERROR (mv) max |
|---|---|---|---|---|---|
| FIRST WINDOW | | | | | |
| Cl | −0.65 | 0.65 | −200 | +100 | 0.2 |
| K | −0.25 | 1.0 | −250 | +100 | 0.2 |
| Na | 0.0 | 1.0 | −250 | +100 | 0.2 |
| BUN[a] | −0.65 | 0.65 | −200 | +100 | 0.2 |
| Gluc[b] | −0.02[c] | 0.02[c] | 0.2[d] | 3[d] | 0.015[d] |
| SECOND WINDOW | | | | | |
| Cl | −0.65 | 0.65 | −200 | +100 | 0.2 |
| K | −0.25 | 1.0 | −250 | +100 | 0.2 |
| Na | 0.0 | 1.0 | −250 | +100 | 0.2 |
| BUN[a] | −1.0 | 1.0 | −200 | +100 | 0.4 |
| Gluc[b] | −0.1[c] | 0.1[c] | 0.05[d] | 32[d] | 0.015[d] |

[a]Cl, K, Na and BUN stands for chloride, potassium, sodium and Blood Urea Nitrogen sensors, respectively.
[b]Gluc stands for Glucose sensor.
[c]This value is in units of nA/s.
[d]This value is in nA.

In the present instance, the limit on the difference (in mV/s) between the value of the slope in each time window is set at a maximum of 0.50, 0.30, 0.30 and 1.00 for the chloride, potassium, sodium and BUN sensors, respectively. The observed waveform for the second fluid, such as glucose, in contact with the microfabricated amperometric sensors can exhibit a maximum or minimum value; consequently a linear/mean fit is preferred.

If one of the above tests indicates that the measurement is out of range, all the measurements generated by a particular sensor are discarded as unreliable. However, the present method provides for error recovery of corrupt data. Accordingly, if an error is detected at test 43, the method flow passes to test 44. If no errors are detected, control is transferred to block 47, where the sensors' responses are determined.

Test 44 determines whether a previous attempt to correct errors has already been made. At this step, a variable "FIRST_TIME" is incremented by one. (FIRST_TIME is initialized to zero at the beginning of the Data Analysis for each time window.) A value of FIRST_TIME that is greater than 1 indicates that a previous attempt to correct errors has been made. Because the flow returned subsequently to test 44, error recovery failed once and should not be repeated. In this case, method flow passes to block 46, where the "FAILED" bit is set to indicate that this particular measurement has failed, and that the only further processing remaining for such sensor involves displaying an error message at block 51. Otherwise, the value of FIRST_TIME is one and the flow passes to block 46, where error recovery is attempted.

Error recovery can be implemented in a variety of ways. For example, noise and spikes in the data can be eliminated by known digital techniques, such as median filters and the like described previously, i.e., the reevaluation of observed values (See, e.g., p. 29.) Another method may involve the interpolation of a curve on the basis of the first several points of a given time window and the rejection of those points that deviate significantly from the interpolation. In most cases, it may be desirable to collect more data points than that required for a given time window, so that error recovery may be accomplished by selecting an alternative time window set. From error recovery at block 46, method flow turns back to block 42 where the points of the corrected data set are interpolated and new slopes and errors of approximation are computed.

If collected data passes all the integrity tests, the control is transferred to block 47 where the sensors' responses are determined by relating measurements in the first (calibrant) time window to those in the second (sample) time window. For potentiometric sensors, the analytical value of interest is the delta response, which is the difference between the amplitudes measured at a selected point of an analyte and calibrant response curves. For amperometric sensors, the delta response corresponds to the ratio of the respective amplitudes. As mentioned above, the data acquisition is performed while the sensors exhibit a monotonic wet-up response. In this instance, the responses are measured in time windows which are selected such that linear interpolations are sufficiently accurate to describe the response drifts. Consequently, linear approximations of block 42 can be reliably projected forward and backward in time to compare each sensor's response to the fluid change. As mentioned previously, nth order approximations can also be used for this purpose.

The particular sensor's delta response is then calculated in one of the many different ways including, but not limited to, a Linear/Linear delta, Linear/Mean delta, Mean/Mean delta, Mean/Linear delta, Maximum/Linear delta, Linear/Maximum delta, Linear/Minimum delta and Minimum/Linear delta approaches. In the Linear/Linear case, the fit to the first window is extrapolated forward to an estimated fluid transition point, i.e., the midpoint between the first window and the second window. The fit to the second window (sample) is extrapolated backward to the same estimated transition point. The difference between these extrapolations is the particular sensor's delta response. In the Linear/Mean approach, the linear fit to the calibrant is extrapolated forward to the midpoint value of the sample window and compared to the midpoint value of the sample response curve. In the Mean/Linear approach the previous sequence is reversed. In the Mean/Mean approach, the delta response is the difference between the midpoint of the sample window and the midpoint value of the calibrant window. The Linear/Maximum, Maximum/Linear, Linear/Minimum and Minimum/Linear methods are analogous to Linear/Mean and Mean/Linear methods, except that the mean value is replaced by the maximum or minimum value of the corresponding time window. On the basis of routine experimentation, one of the above methods can be found more desirable than the others for obtaining a more accurate measure of the concentration of a particular analyte when compared to a reference method of analysis. Presently, the Linear/Linear method is found to be superior for the potassium, sodium and chloride sensors. A Linear/Mean method is best for the present embodiment of the glucose and urea sensors.

After the delta responses are computed for each sensor, the flow passes to block 48. At block 48, the response of the reference electrode is subtracted from the delta response determined in block 47. At this stage, certain corrections are made for a slight response of the reference electrode due to matrix effects and differences in ionic strength of the fluids. Next, the flow passes to block 49, where, for potentiometric sensors, Equation 1 and coefficients derived from Equation 2, as described above, are applied to determine analyte concentrations. For amperometric sensors, Equation 3 is applied. Then, at block 50, the results are appropriately scaled in order to derive standardized values. Finally, block 51 provides a display of the calculated concentrations or a display of an appropriate message if aberrant values are found.

The preceding example is presented solely to illustrate a method for practicing the invention and should not be construed as limiting the invention in any way. Doubtless, other embodiments may be conceived which would not depart significantly from the spirit and of the present invention, which scope is defined by the following claims.

What is claimed is:

1. A method of determining the concentration of a preselected analyte species present in a sample fluid comprising:
   (a) providing an external computational means, a reference electrode and at least one substantially dry-stored microfabricated sensor capable of exhibiting a response to changes in the concentration of a preselected analyte species;
   (b) establishing electrical contact between said sensor, reference electrode and external computational means;
   (c) contacting said sensor and reference electrode with a calibrant fluid;
   (d) performing a first signal measurement in a first time window in the presence of said calibrant fluid before said sensor attains full equilibrated wet-up;
   (e) displacing said calibrant fluid after performing said first signal measurement;
   (f) contacting said sensor and reference electrode with a sample fluid;
   (g) performing a second signal measurement in a second time window in the presence of said sample fluid before said sensor attains full equilibrated wet-up; and
   (h) relating said first and second signal measurements to determine the concentration of said preselected analyte species in said sample fluid.

2. A method of determining the concentration of a preselected analyte species present in a sample fluid comprising:
   (a) providing at least one microfabricated potentiometric sensor sensitive to changes in the concentration of a preselected analyte species, a reference electrode capable of sustaining a well-behaved reference potential for a period of time sufficient to permit the completion of at least two signal measurement before said sensor attains full equilibrated wet-up and external computational means, which sensor and reference electrode have been stored substantially dry;
   (b) establishing electrical contact between said sensor, reference electrode and external computational means;
   (c) contacting said sensor and reference electrode with a calibrant fluid;
   (d) performing a first signal measurement in a first time window in the presence of said calibrant fluid before said sensor attains full equilibrated wet-up;
   (e) displacing said calibrant fluid after performing said first signal measurement;
   (f) contacting said sensor and said reference electrode with a sample fluid;
   (g) performing a second signal measurement in a second time window in the presence of said sample fluid before said sensor attains full equilibrated wet-up; and
   (h) relating said first and second signal measurements to determine the concentration of said preselected analyte species in said sample fluid.

3. A method of determining the concentration of a plurality of different preselected analyte species present in a sample fluid comprising:
   (a) providing an array of microfabricated potentiometric and amperometric sensors, each sensitive to changes in the concentration of different preselected analyte species, and external computational means, which array comprises individual sensors and at least two reference electrodes capable of sustaining a well-behaved reference potential for a period of time sufficient to permit the completion of at least two sets of signal measurements before said sensors attain full equilibrated wet-up, one reference electrode being connected to said potentiometric sensors when the other reference electrode is connected to said amperometric sensors, and each of which sensors has been stored substantially dry;
   (b) establishing electrical contact between said array of sensors and external computational means;

(c) contacting said array of sensors with a calibrant fluid;

(d) performing a first set of signal measurements in a first time window in the presence of said calibrant fluid before said sensor attains full equilibrated wet-up;

(e) displacing said calibrant fluid after performing said first set of signal measurements;

(f) contacting said array of sensors with a sample fluid;

(g) performing a second set of signal measurements in a second time window in the presence of said sample fluid before said sensor attains full equilibrated wet-up; and (h) relating said first and second sets of signal measurements to determine the concentration of a plurality of the different preselected analyte species in said sample fluid.

4. A method of determining the ratio of the concentrations of a preselected analyte species present in two fluids comprising:

(a) providing at least one microfabricated amperometric sensor sensitive to changes in the concentration of a preselected analyte species, a reference electrode capable of sustaining a well-behaved reference potential for a period of time sufficient to permit the completion of at least two signal measurements before said sensors attain full equilibrated wet-up and external computational means, which sensor and reference electrode have been stored substantially dry;

(b) establishing electrical contact between said sensor, reference electrode and external computational means;

(c) contacting said sensor and reference electrode with a first fluid;

(d) performing a first signal measurement in a first time window in the presence of said first fluid before said sensor attains full equilibrated wet-up;

(e) displacing said first fluid after performing said first signal measurement;

(f) contacting said sensor and said reference electrode with a second fluid;

(g) performing a second signal measurement in a second time window in the presence of said second fluid before said sensor attains full equilibrated wet-up; and (h) relating said first and second signal measurements to determine the ratio of the concentrations of said preselected analyte species in said first and second fluids.

5. A method of determining the ratio of the concentrations of a preselected analyte species present in two fluids comprising:

(a) providing at least one dry-stored microfabricated sensor capable of exhibiting a response to changes in the concentration of a preselected analyte species, which response is fast relative to the monotonic wet-up behavior of said sensor when contacted with a fluid;

(b) providing a dry-stored microfabricated reference electrode capable of sustaining a well-behaved reference potential for a period of time sufficient to permit the completion of at least two signal measurements before said sensor attains fully equilibrated wet-up and exhibiting a monotonic wet-up behavior which is similar to that exhibited by said sensor when contacted with a fluid;

(c) establishing electrical contact between said sensor, reference electrode and external computational means;

(d) contacting said sensor and reference electrode with a first fluid;

(e) performing a first signal measurement in a preselected first tie window in the presence of said first fluid before said sensor and reference electrode attain full equilibrated wet-up;

(f) displacing said first fluid after performing said first signal measurement;

(g) contacting said sensor and reference electrode with a second fluid;

(h) performing a second signal measurement in a preselected second time window in the presence of said second fluid before said sensor and reference electrode attain full equilibrated wet-up;

(i) relating the first and second signal measurements to determine the ratio of the concentrations of said analyte species in said first and second fluids by a computational method which distinguishes the relatively fast response of the sensor to changes in the concentration of said preselected analyte from the slower monotonic wet-up behavior of said sensor and reference electrode.

6. The method of claim 1, 2 or 3 in which the order by which said sensor, reference electrode or array thereof is contacted with said calibrant and sample fluids is reversed.

7. The method of claim 6 in which said first and second signal measurements or sets thereof are performed in the presence of said sample and calibrant fluids, respectively.

8. The method of claim 4 or 5 in which said first fluid is a calibrant fluid.

9. The method of claim 8 in which said second fluid is sample fluid.

10. The method of claim 4 or 5 in which said first fluid is sample fluid.

11. The method of claim 10 in which said second fluid is calibrant

12. The method of claim 1, 2, 3, 4 or 5 which further comprises providing a conductivity sensor capable of measuring the conductivity of a fluid in contact therewith.

13. The method of claim 1, 2 or 3 which further comprises performing a first conductivity measurement in the presence of said calibrant fluid.

14. The method of claim 4 or 5 which further comprises performing a first conductivity measurement in the presence of said first fluid.

15. The method of claim 13 which further comprises performing a second conductivity measurement in the presence of said sample fluid.

16. The method of claim 14 which further comprises performing a second conductivity measurement in the presence of said second fluid.

17. The method of claim 13 in which said first conductivity measurement is performed prior to performing said first signal measurement or set thereof.

18. The method of claim 14 in which said first conductivity measurement is performed prior to performing said first signal measurement.

19. The method of claim 15 in which said second conductivity measurement is performed after performing said second signal measurement or set thereof.

20. The method of claim 16 in which said second conductivity measurement is performed after performing said second signal measurement.

21. The method of claim 3 or 4 which further comprises activating said amperometric sensor or array thereof.

22. The method of claim 21 in which activating said amperometric sensor comprises subjecting said amperometric sensor to a series of potential changes in the presence of said calibrant or first fluid.

23. The method of claim 22 in which said potential changes comprises cycling the applied potential between values of opposite sign relative to said reference electrode.

24. The method of claim 22 in which said series of potential changes includes a first group which comprises at least ten repetitions of a cycle in which the applied potential is maintained at a first value and then is switched to a second value of equal magnitude but of opposite sign as said first value.

25. The method of claim 24 in which said series of potential changes further includes a second group which comprises at least five repetitions of a cycle in which the applied potential is maintained at a first value and then is switched to a second value of equal magnitude but of opposite sign as said first value.

26. The method of claim 25 in which said series of potential changes further includes a third group which comprises at least five repetitions of a cycle in which the applied potential is maintained at a first value and then is switched to a second value of equal magnitude but of opposite sign as said first value.

27. The method of claim 24 in which the application of said first group is commenced within about one second after said calibrant or first fluid comes into contact with said amperometric sensor.

28. The method of claim 25 in which the application of said second group is commenced within about twelve seconds after said calibrant or first fluid comes into contact with said amperometric sensor.

29. The method of claim 26 in which the application of said third group is commenced within about twenty seconds after said calibrant or first fluid comes into contact with said amperometric sensor.

30. The method of claim 25 in which said first value for said first and second groups is about +1000 mV.

31. The method of claim 26 in which said first value for said third group is within double the magnitude of the operating potential of said amperometric sensor.

32. The method of claim 3 which further comprises:
providing a conductivity sensor capable of measuring the conductivity of a fluid in contact therewith,
activating said amperometric sensor in the presence of said calibrant fluid, and
performing a first conductivity measurement in the presence of said calibrant fluid, after activating said amperometric sensor but before performing any set of signal measurements.

33. The method of claim 32 which further comprises performing a second conductivity measurement in the presence of said sample fluid, after performing all sets of signal measurements.

34. The method of claim 1, 2, 3, 4 or 5 in which said signal measurements or sets thereof are performed within about 2 minutes.

35. The method of claim 1, 2, 3, 4 or 5 in which the end of said first time window and the beginning of said second time window are separated by about three to about six seconds.

36. The method of claim 1, 2, 3, 4 or 5 in which the end of said first time window and the beginning of said second time window are separated by no more than about ten seconds.

37. The method of claim 1, 2, 3, 4 or 5 in which the duration of said time windows is about five to about fifteen seconds.

38. The method of claim 3 in which one of said reference electrodes is replaced with a counter electrode,
that the remaining reference electrode is available to both of said potentiometric and amperometric sensors and said counter electrode is dedicated to said amperometric sensors.

39. The method of claim 1, 2, or 3 in which the displacement of said calibrant fluid is carried out by the introduction of said sample fluid.

40. The method of claim 39 in which the displacement of said calibrant fluid with said sample fluid is carried out with an air segment separating said fluids.

41. The method of claim 4 or 5 in which the displacement of said first fluid is carried out by the introduction of said second fluid.

42. The method of claim 41 in which the displacement of said first fluid with said second fluid is carried out with an air segment separating said fluids.

43. The method of claim 1 in which performing said signal measurements comprises acquiring a preselected number of data points over the time period of said time windows.

44. The method of claim 43 in which acquiring said data points comprises:
(a) collecting a first preselected fraction of said data points in a first sliding window, which first sliding window comprises a corresponding fraction of said time window; and
(b) collecting additional preselected fractions of said data points in subsequent sliding windows until every data point in said time window is included in at least one sliding window.

45. The method of claim 44 in which said first and subsequent sliding windows are of equal duration.

46. The method of claim 44 in which said first and additional preselected fractions contain an equal number of data points.

47. The method of claim 44 in which collecting additional fractions of said data points comprises including at least one new point of data in said first sliding window to form a subsequent sliding window.

48. The method of claim 44 in which collecting additional fractions of said data points comprises removing at least the earliest point of data collected in said first sliding window and adding to the remaining points of data at least one new point of data to form a subsequent sliding window.

49. The method of claim 44 which further comprises designating one of said preselected fractions as forming a basis set of data points and determining its characteristics.

50. The method of claim 49 which further comprises comparing the characteristics of said basis set of data points with the characteristics of the remaining preselected fractions.

51. The method of claim 50 in which one of said characteristics includes the slope of each preselected fraction in its respective sliding window.

52. The method of claim 50 which further comprises detecting the presence of aberrant data points on the basis of such comparisons.

53. The method of claim 52 which further comprises counteracting the deleterious effects of said aberrant data points if the presence of such points has been detected.

54. The method of claim 53 in which counteracting the deleterious effects of said aberrant data points comprises performing a step selected from the group consisting of utilizing median filter techniques, eliminating the data points which lie outside the desired range and interpolating the remaining data points, utilizing digital filter techniques or discarding the sliding window which contains said aberrant data points.

55. The method of claim 1 which further comprises comparing the slope of the data points in a particular time window to a range of expected values to determine the integrity of the corresponding signal measurement.

56. The method of claim 1 which further comprises comparing the difference between the slope of the data points in said first time window and the slope of the data points in said second time window to a range of preselected limiting values to determine the integrity of said signal measurements.

57. The method of claim 1 which further comprises comparing the mean value of the data points in a particular time window to a range of expected values to determine the integrity of said signal measurement.

58. The method of claim 1 which further comprises comparing the deviation of the data points in a particular time window from the linear interpolation of said data points to a range of preselected limiting values to determine the integrity of said signal measurement.

59. The method of claim 1, 2, 3, 4 or 5 in which relating said signal measurements comprises:

(a) interpolating the data points in said first time window;

(b) interpolating the data points in said second time window;

(c) extrapolating said first time window interpolation forward to a position located between said first and second time windows;

(d) extrapolating said second time window interpolation backward to said position; and (e) calculating the ratio of the values obtained from said extrapolations, from which ratio the concentration of said preselected analyte species can be determined.

60. The method of claims 2 or 3 in which said calibrant fluid is comprised of an aqueous liquid or a wet gas.

61. The method of claim 22 in which said potential changes are applied in the form of pulses, incremental steps, sine waves, linear sweeps or combinations thereof.

62. The method of claim 1, 2, 3, 4 or 5 in which at least two signal measurements are performed in each of said first and second time windows, one of said signal measurements being carried out at a first applied potential and the other being carried out at a second applied potential.

63. The method of claim 62 in which said signal measurement includes measuring the current.

64. The method of claim 62 in which said first and second applied potentials lie in the range of about 100 to about 300 mV.

65. The method of claim 62 in which one of said signal measurements in said first time window is carried out at an applied potential of about 125 mV and the other measurement is carried out at about 225 mV.

66. The method of claim 65 in which one of said signal measurements in said second time window is carried out at an applied potential of about 225 mV and the other measurement is carried out at about 125 mV.

67. The method of claim 62 which further comprises determining the slope of the line defined by at least two points on a signal versus applied potential curve, which points are obtained from said signal measurements performed at each of said time windows.

68. The method of claim 67 in which relating said signal measurements involves comparing the slopes of said lines obtained from said time windows to determine the concentration of said preselected analyte species.

* * * * *